United States Patent
Bassaganya-Riera et al.

(10) Patent No.: US 12,145,921 B2
(45) Date of Patent: Nov. 19, 2024

(54) AROMATIC IMMUNOREGULATORY COMPOUNDS FOR TREATMENT OF INFLAMMATORY DISEASES

(71) Applicant: NIMML INSTITUTE, Blacksburg, VA (US)

(72) Inventors: Josep Bassaganya-Riera, Blacksburg, VA (US); Andrew J. Leber, Christiansburg, VA (US); Raquel Hontecillas, Blacksburg, VA (US)

(73) Assignee: NIMML Institute, Blacksburg, VA (US)

( * ) Notice: Subject to any disclaimer, the term of this patent is extended or adjusted under 35 U.S.C. 154(b) by 0 days.

(21) Appl. No.: 17/960,039

(22) Filed: Oct. 4, 2022

(65) Prior Publication Data
US 2023/0192648 A1 Jun. 22, 2023

Related U.S. Application Data

(60) Provisional application No. 63/291,891, filed on Dec. 20, 2021.

(51) Int. Cl.
| | |
|---|---|
| C07D 401/12 | (2006.01) |
| A61K 9/00 | (2006.01) |
| A61K 9/70 | (2006.01) |
| A61P 37/02 | (2006.01) |
| C07D 401/14 | (2006.01) |
| C07D 413/14 | (2006.01) |
| C07D 417/14 | (2006.01) |

(52) U.S. Cl.
CPC .......... *C07D 401/12* (2013.01); *A61K 9/0029* (2013.01); *A61K 9/7023* (2013.01); *A61P 37/02* (2018.01); *C07D 401/14* (2013.01); *C07D 413/14* (2013.01); *C07D 417/14* (2013.01)

(58) Field of Classification Search
CPC .............................. C07D 401/00; C07D 413/00
See application file for complete search history.

(56) References Cited

U.S. PATENT DOCUMENTS

| | | | |
|---|---|---|---|
| 4,922,052 A | 5/1990 | Shimizu et al. | |
| 4,967,009 A | 10/1990 | Shimizu et al. | |
| 6,300,534 B1 | 10/2001 | Konishi et al. | |
| 7,396,943 B2 | 7/2008 | Benesh et al. | |
| 8,859,546 B2 | 10/2014 | Vasudevan et al. | |
| 10,246,451 B2 * | 4/2019 | Biediger | A61P 35/00 |
| 2013/0178520 A1 * | 7/2013 | McCafferty | C07C 217/74 |
| | | | 514/466 |
| 2020/0109129 A1 * | 4/2020 | Stansfield | C07D 405/14 |
| 2020/0190017 A1 | 6/2020 | Blagg et al. | |

FOREIGN PATENT DOCUMENTS

| | | | | |
|---|---|---|---|---|
| CN | 113754591 A | * | 12/2021 | ............. A61P 19/02 |
| WO | 2005012298 A1 | | 2/2005 | |
| WO | 2015061247 A2 | | 4/2015 | |
| WO | 2020198537 A1 | | 1/2020 | |
| WO | 2021129817 A1 | | 1/2021 | |

OTHER PUBLICATIONS

Hebert et al. Synthesis of Highly Functionalized Triarylbismuthines by Functional Group Manipulation and Use in Palladium- and Copper-Catalyzed Arylation Reactions, JOC, May 2016, pp. 5401-5416. (Year: 2016).*
CN 1137545914 Machine Translation (Year: 2021).*
CN 113754591A Machine Translation (Year: 2021).*
"Pubchem CID 14882414", Create date: Feb. 9, 2007 (Feb. 9, 2007), entire document.
International Search Report and Written Opinion received in PCT/US22/45711, mailed on Feb. 27, 2023 (9 pages).

* cited by examiner

*Primary Examiner* — Sarah Pihonak
*Assistant Examiner* — Mikhail O'Donnel Robinson
(74) *Attorney, Agent, or Firm* — Gendloff IP; Elie Gendloff

(57) ABSTRACT

Provided is a compound of Formula 1

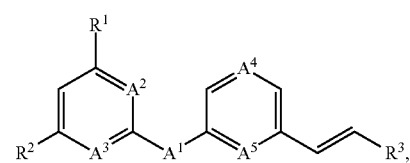

Formula 1 wherein
$A^1$ is selected from $CH^2$, $CHR^4$, $CR^4R^5$, NH, $NR^4$, O, or S;
$A^2$, $A^3$, $A^4$, and $A^5$ are each independently selected from CH, $CR^6$, or N;
$R^1$, $R^2$, $R^3$, $R^4$, $R^5$, $R^6$, when present, are independently hydrogen, hydroxy, acetyl, halo, carboxyl; a substituted or unsubstituted amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O, or S. Also provided is a method of treating a mammal undergoing an inflammatory disease, the method comprising administering the above compound to the mammal in a manner sufficient to reduce the severity of the inflammatory disease.

10 Claims, 18 Drawing Sheets

| ID | Structure | Affinity (kcal/mol) |
|---|---|---|
| NIM-1001-1 | 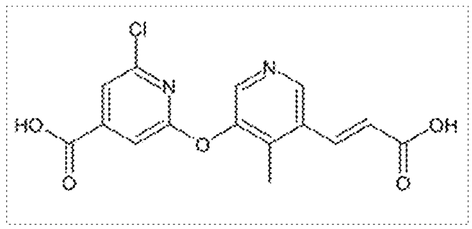 | -7.7 |
| NIM-1001-2 | 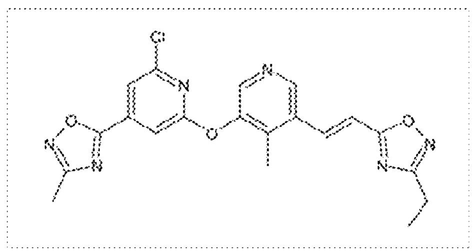 | -9.2 |
| NIM-1001-3 | 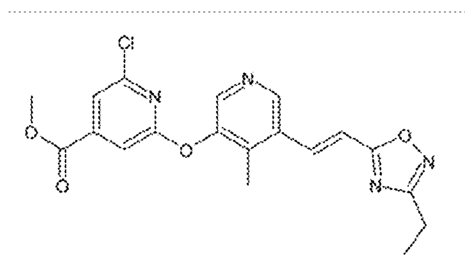 | -8.6 |
| NIM-1001-4 | 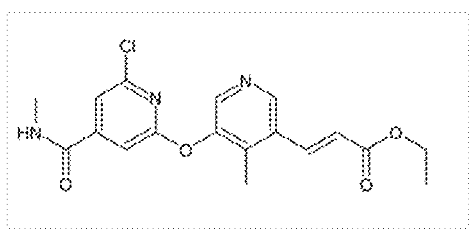 | -8.0 |
| NIM-1001-5 | 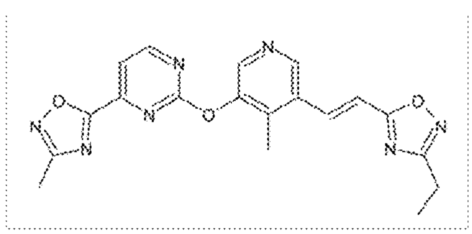 | -9.1 |

| ID | Structure | Affinity (kcal/mol) |
|---|---|---|
| NIM-1001-6 | 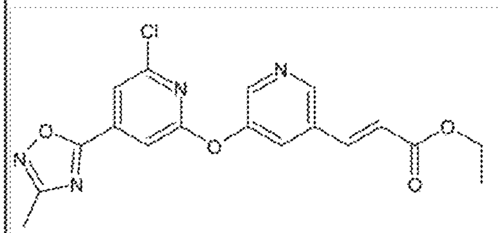 | -8.4 |
| NIM-1001-7 | 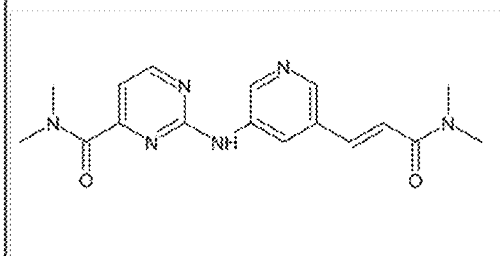 | -8.1 |
| NIM-1001-8 | 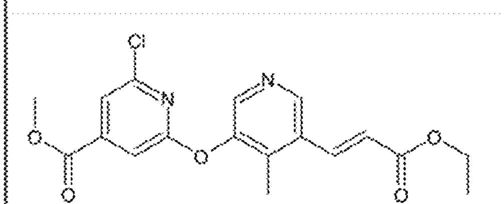 | -8.6 |
| NIM-1001-9 | 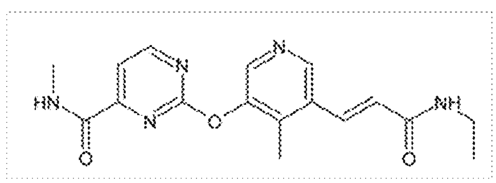 | -8.2 |
| NIM-1001-10 | 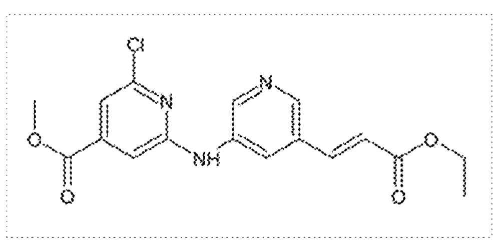 | -7.6 |

| ID | Structure | Affinity (kcal/mol) |
|---|---|---|
| NIM-1001-11 | 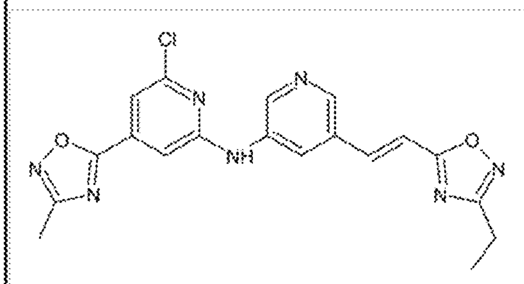 | -8.8 |
| NIM-1001-12 | 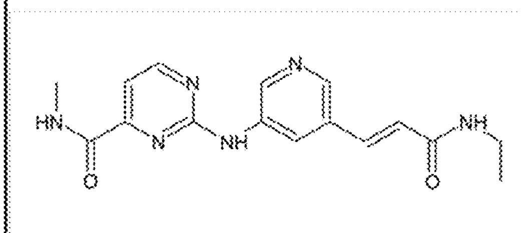 | -7.9 |
| NIM-1001-13 | 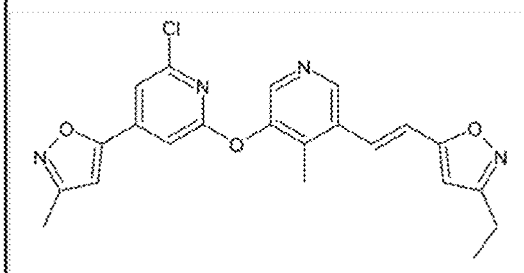 | -8.4 |
| NIM-1001-14 | 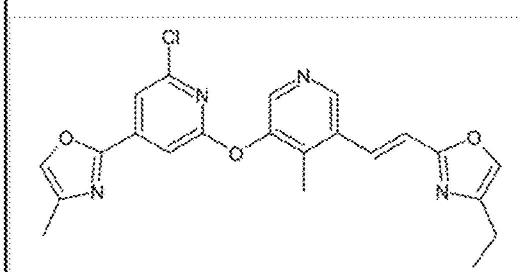 | -8.2 |
| NIM-1001-15 | 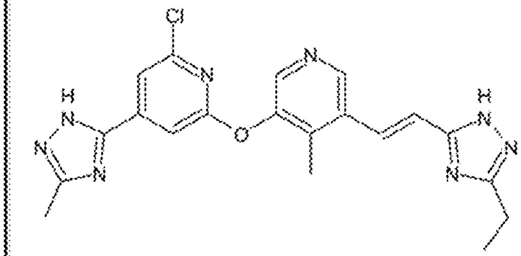 | -8.5 |

| ID | Structure | Affinity (kcal/mol) |
|---|---|---|
| NIM-1001-16 | 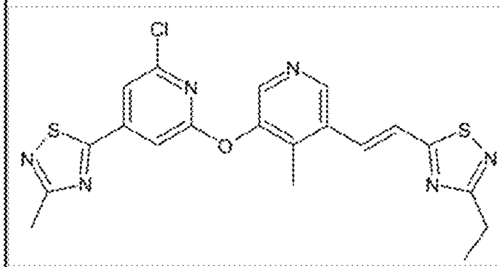 | -9.0 |
| NIM-1001-17 | 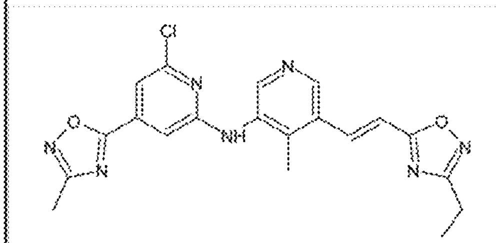 | -9.0 |
| NIM-1001-18 | 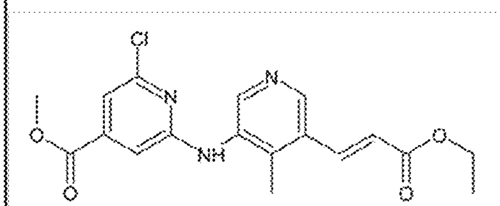 | -7.6 |
| NIM-1001-19 | 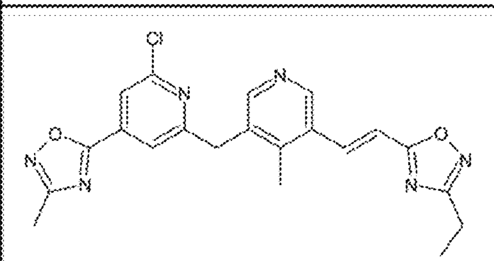 | -9.1 |
| NIM-1001-20 | 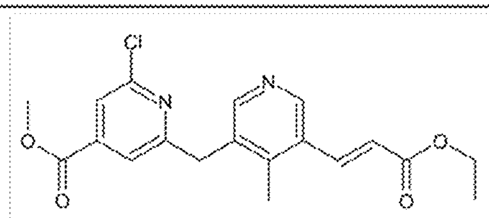 | -7.9 |

FIG. 1D

| ID | Structure | Affinity (kcal/mol) |
|---|---|---|
| NIM-1001-21 | 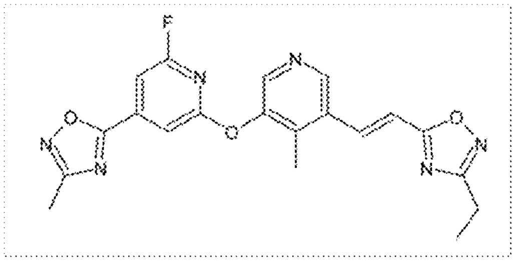 | -9.0 |
| NIM-1001-22 | 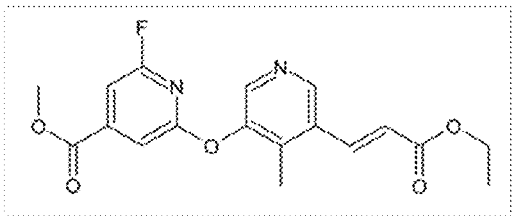 | -7.6 |
| NIM-1001-23 | 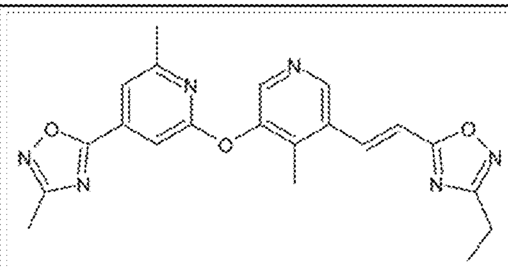 | -8.8 |
| NIM-1001-24 | 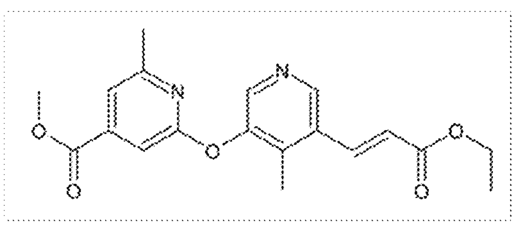 | -7.5 |
| NIM-1001-25 | 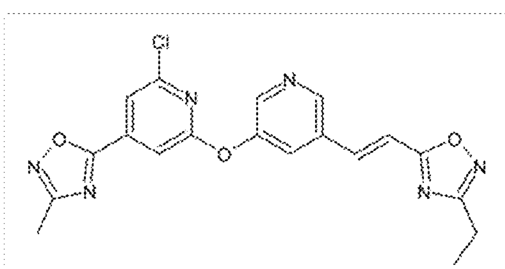 | -8.9 |

FIG. 1E

| ID | Structure | Affinity (kcal/mol) |
|---|---|---|
| NIM-1001-26 | 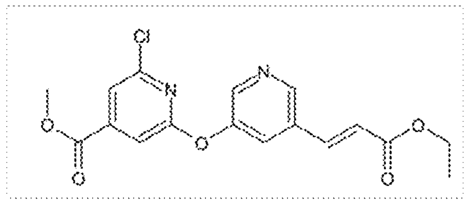 | -7.7 |
| NIM-1001-27 | 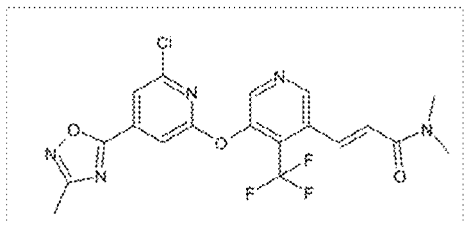 | -9.4 |
| NIM-1001-28 | 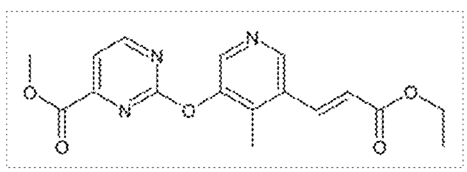 | -7.6 |
| NIM-1001-29 | 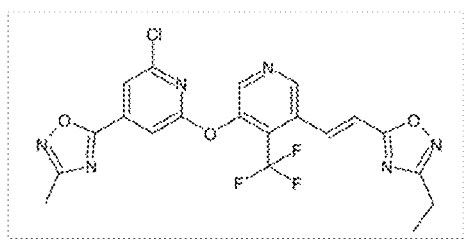 | -9.3 |
| NIM-1001-30 | 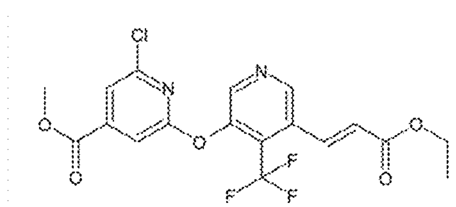 | -9.0 |

| ID | Structure | Affinity (kcal/mol) |
|---|---|---|
| NIM-1001-31 | 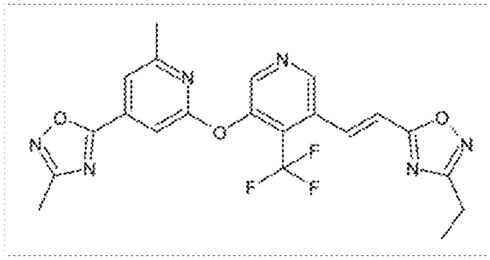 | -9.4 |
| NIM-1001-32 | 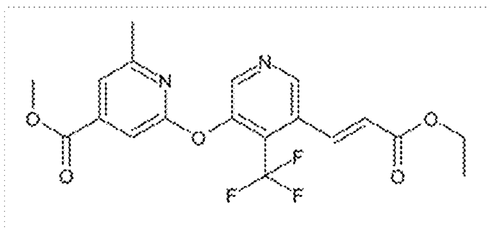 | -7.8 |
| NIM-1001-33 | 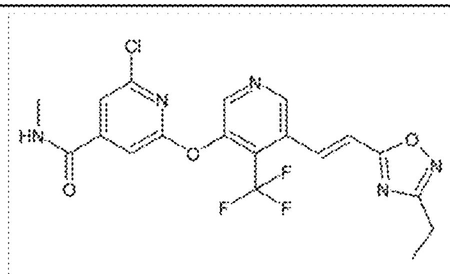 | -9.2 |
| NIM-1001-34 | 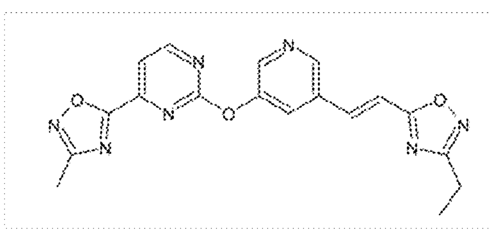 | -8.9 |
| NIM-1001-35 | 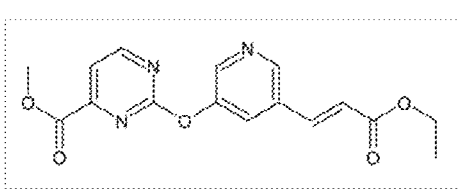 | -7.6 |

FIG. 1G

| ID | Structure | Affinity (kcal/mol) |
|---|---|---|
| NIM-1001-36 | 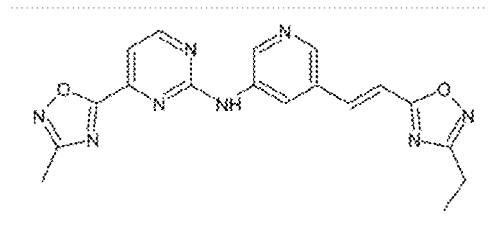 | -9.1 |
| NIM-1001-37 | 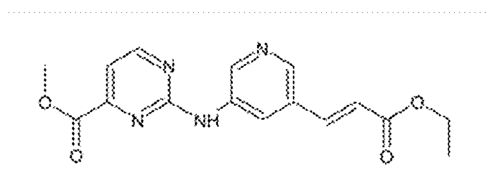 | -7.4 |
| NIM-1001-38 | 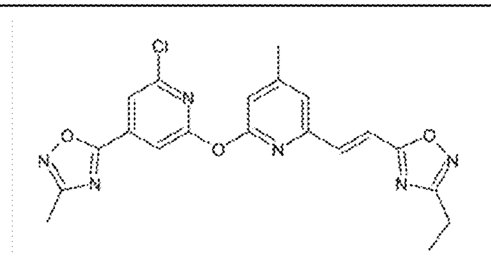 | -9.0 |
| NIM-1001-39 | 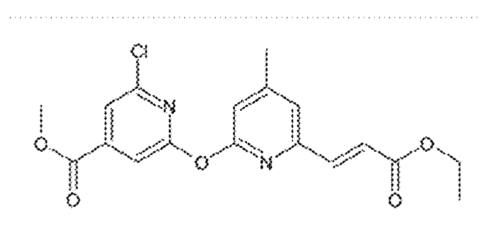 | -7.4 |

AROMATIC IMMUNOREGULATORY COMPOUNDS FOR TREATMENT OF INFLAMMATORY DISEASES

CROSS-REFERENCE TO RELATED APPLICATIONS

This application claims the benefit of U.S. Provisional Application No. 63/291,891, filed Dec. 20, 2021, and incorporated by reference herein in its entirety.

BACKGROUND OF THE INVENTION

(1) Field of the Invention

The present application generally relates to compounds that modulate the mammalian immune system. More specifically, compounds that modulate multiple immune factors and alleviate several diseases are provided.

(2) Description of the Related Art

Dysregulation of the immune system can result in numerous health conditions and disorders including neurodegenerative diseases, complications arising from viral infections, autoimmune diseases, alterations in systemic metabolism. Current strategies to treat these conditions include the blocking of individual cytokines or chemokines and inhibiting key pathway tied to immune activation. Often, these strategies result in loss of response over time or are poorly tolerated with many side effects tied to broad immunosuppression. New strategies have the potential to reach millions of patients.

Recent studies have revealed the ability to modulate immune responses based on cellular metabolism. The relative balance of glucose and lipid metabolism and oxidative and anaerobic pathways differs between cells that promote inflammation and cells that restrict inflammation. There is thus a need for compounds that target receptors and signaling proteins within immune cells that influence this balance. The present invention provides several such compounds.

BRIEF SUMMARY OF THE INVENTION

Provided is a compound of Formula 1

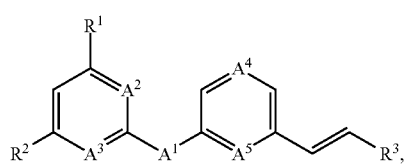

Formula 1 wherein
$A^1$ is selected from $CH_2$, $CHR^4$, $CR^4R^5$, NH, $NR^4$, O, or S;
$A^2$, $A^3$, $A^4$, and $A^5$ are each independently selected from CH, $CR^6$, or N;
$R^1$, $R^2$, $R^3$, $R^4$, $R^5$, $R^6$, when present, are independently hydrogen, hydroxy, acetyl, halo, carboxyl; a substituted or unsubstituted amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O, or S.

Also provided is a method of treating a mammal undergoing an inflammatory disease, the method comprising administering the above compound to the mammal in a manner sufficient to reduce the severity of the inflammatory disease.

BRIEF DESCRIPTION OF THE SEVERAL VIEWS OF THE DRAWINGS

FIG. 1D is structures and binding affinities for compounds NIM-1001-16 to NIM-1001-20.
FIG. 1E is structures and binding affinities for compounds NIM-1001-21 to NIM-1001-25.
FIG. 1G is structures and binding affinities for compounds NIM-1001-31 to NIM-1001-35.

DETAILED DESCRIPTION OF THE INVENTION

Figure 1A:
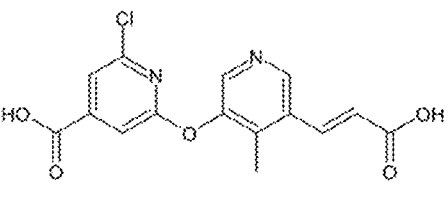
FIG. 1A is structures and binding affinities for compounds NIM-1001-1 to NIM-1001-5.
Figure 1A:
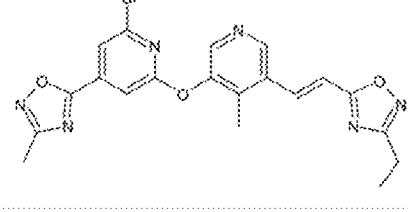
Figure 1A:
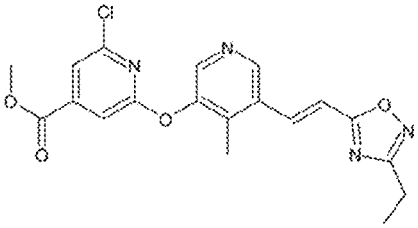
Figure 1A:
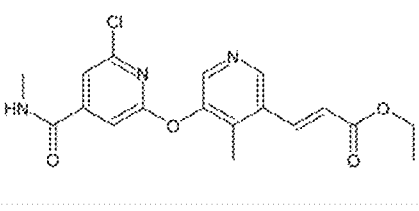
Figure 1A:
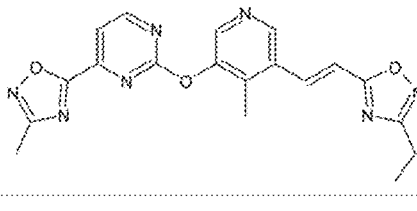
Figure 1B:
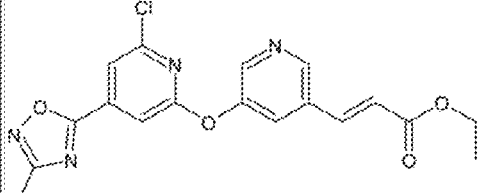
FIG. 1B is structures and binding affinities for compounds NIM-1001-6 to NIM-1001-10.
Figure 1B:
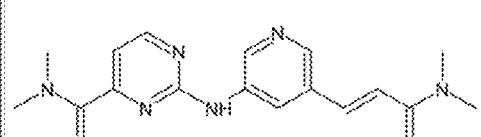
Figure 1B:
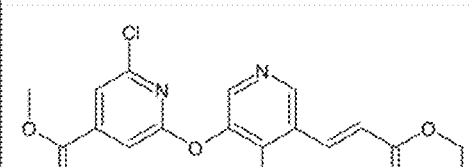
Figure 1B:
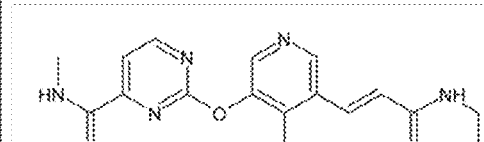
Figure 1B:
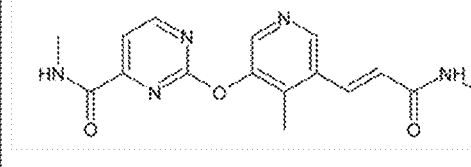
Figure 1C:
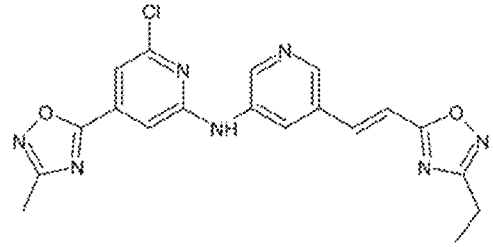
FIG. 1C is structures and binding affinities for compounds NIM-1001-11 to NIM-1001-25.
Figure 1C:
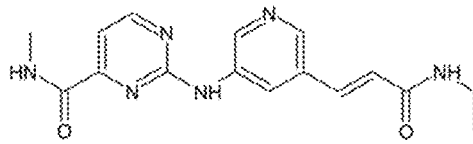
Figure 1C:
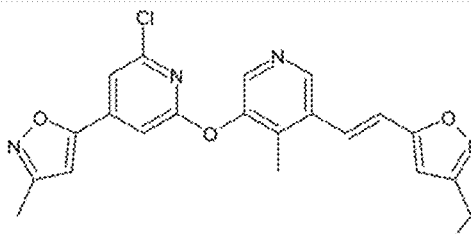
Figure 1C:
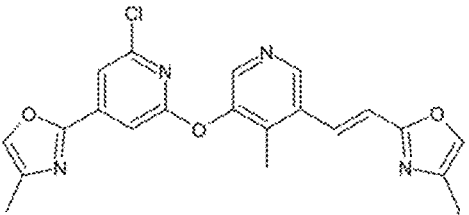
Figure 1C:
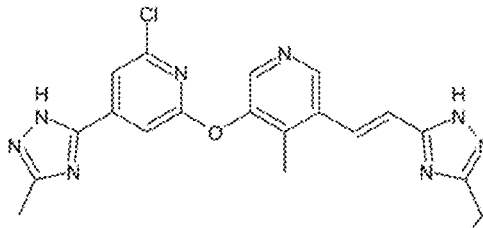
Figure 1F:
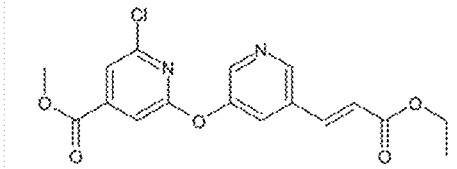
FIG. 1F is structures and binding affinities for compounds NIM-1001-26 to NIM-1001-30.
Figure 1F:
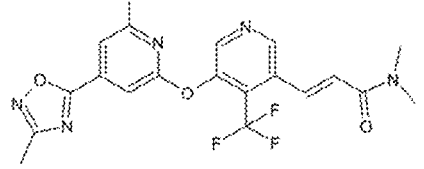
Figure 1F:
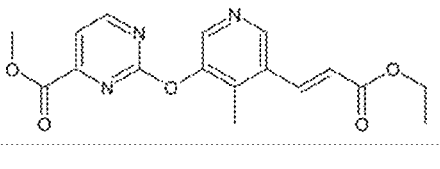
Figure 1F:
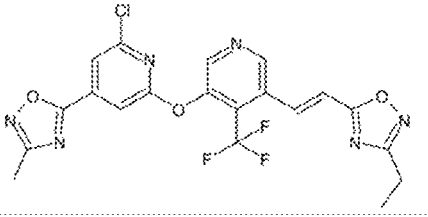
Figure 1F:
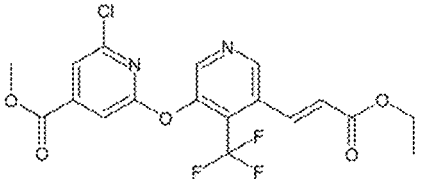
Figure 1H:
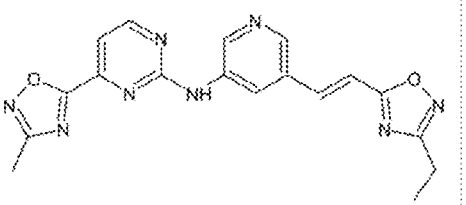
FIG. 1H is structures and binding affinities for compounds NIM-1001-36 to NIM-1001-39.
Figure 1H:
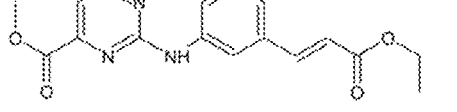
Figure 1H:
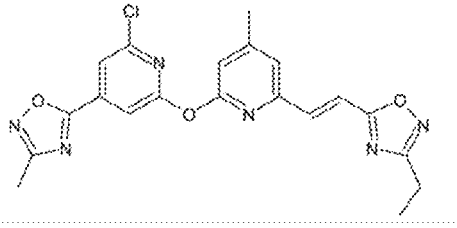
Figure 1H:
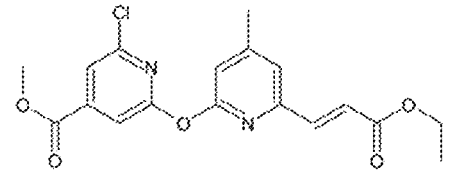

The present invention provides compounds that have been developed by novel medicinal chemistry approaches (Example 1), screened using in silico and in vitro approaches to confirm binding, and validated to be biologically active in in vivo models of disease. Therapeutic use of these compounds may result in an induction or maintenance of beneficial responses in various disease conditions, including but not limited to, inflammatory or immune-mediated diseases, such as psoriasis, systemic lupus erythematosus, multiple sclerosis, inflammatory bowel disease, diabetes or non-alcoholic steatohepatitis, infectious diseases of bacterial, fungal and viral origin, and disorders of the cardiovascular and central nervous systems including atherosclerosis, Alzheimer's disease and Parkinson's disease.

In some embodiments, the present invention is directed to a compound of Formula 1

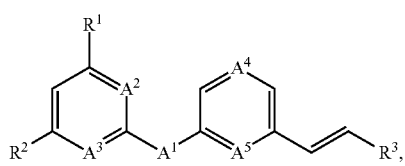

Formula 1 wherein $A^1$ is selected from $CH_2$, $CHR^4$, $CR^4R^5$, NH, $NR^4$, O, or S;

$A^2$, $A^3$, $A^4$, and $A^5$ are each independently selected from CH, $CR^6$, or N;

$R^1$, $R^2$, $R^3$, $R^4$, $R^5$, $R^6$, when present, are independently hydrogen, hydroxy, acetyl, halo, carboxyl; a substituted or unsubstituted amino, alkyl, alkoxy, carboxyalkyl, alkylamide, acyl, acylamino aryl, arylalkyl, heteroalkyl, heteroalkoxy, heterocarboxyalkyl, heteroacyl, heteroacylamino, heteroaryl, or heteroarylalkyl; or a substituted or unsubstituted five-membered heterocycle where any member of the given ring may be C, N, O, or S.

In some of these embodiments, $A^1$ is O, NH, or $CH_2$.

In other embodiments, $A^2$ is N.

In additional embodiments, $A^3$ is CH or N.

In further embodiments, $A^4$ is N or $CHCH_3$.

In other embodiments, $A^5$ is CH, $CCH_3$, $CCF_3$, or N.

In additional embodiments, $R^1$ is not present or is Cl, F, or $CH_3$.

In further embodiments, $R^2$ is COOH, $COOCH_3$, $CONHCH_3$, $CON(CH_3)_2$,

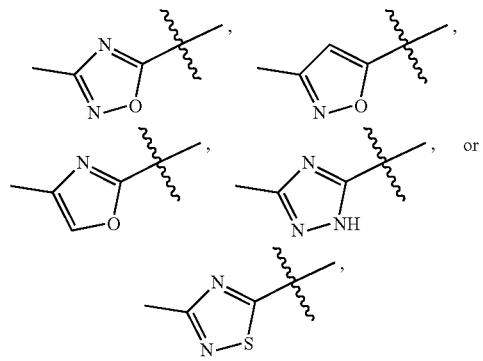

As used herein, "⤳" indicates a bond that is covalently bound to Formula 1 at an R group by crossing that bond.

In other embodiments, $R^3$ is COOH, $COOCH_2CH_3$, $CON(CH_3)_2$, $CONHCH_2CH_3$,

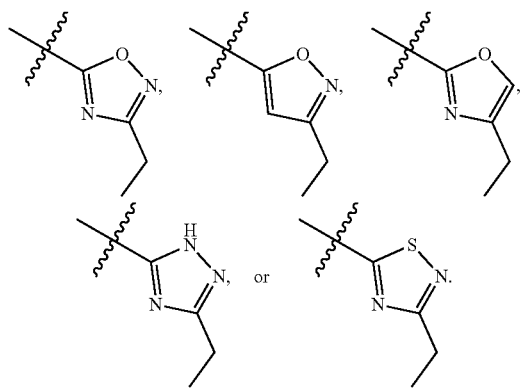

In specific embodiments, the compound is any one of Compounds NIM-1001-1 to NIM-1001-39:

NIM-1001-1
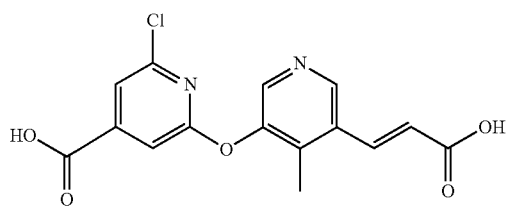
NIM-1001-2
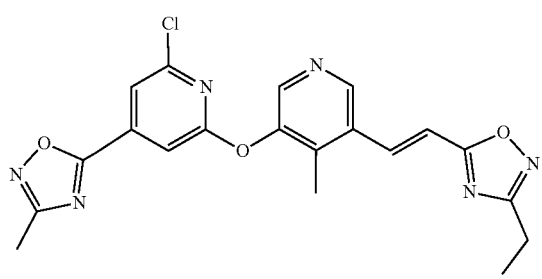
NIM-1001-3
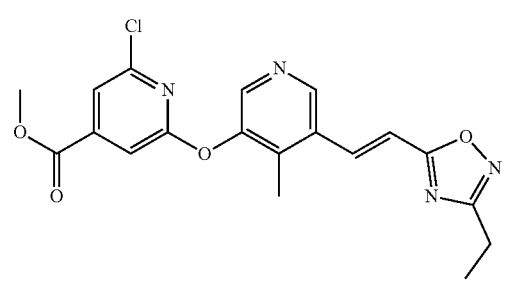
NIM-1001-4
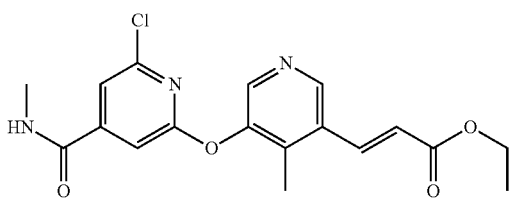
NIM-1001-5
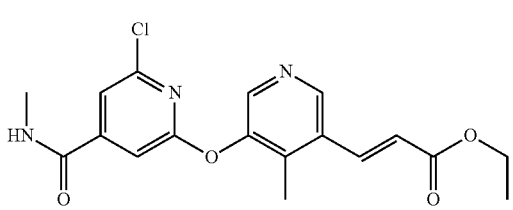
NIM-1001-6
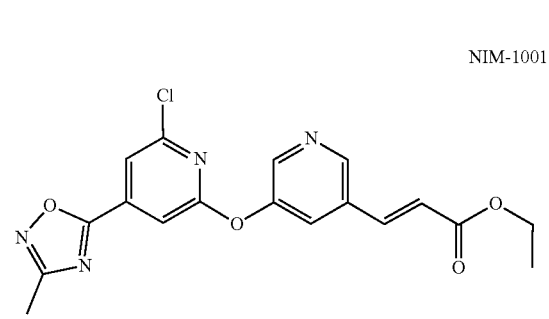
-continued
NIM-1001-7
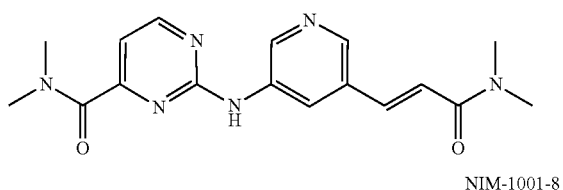
NIM-1001-8
NIM-1001-9
NIM-1001-10
NIM-1001-11
NIM-1001-12
NIM-1001-13
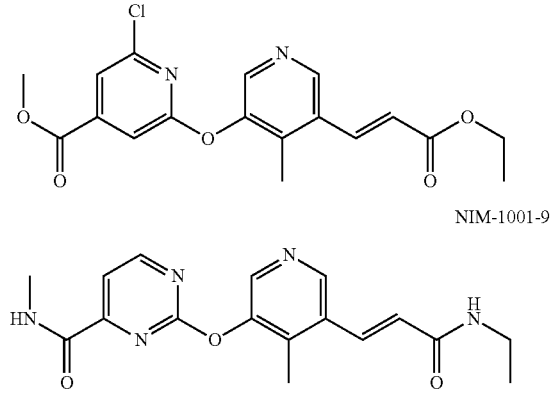

NIM-1001-14
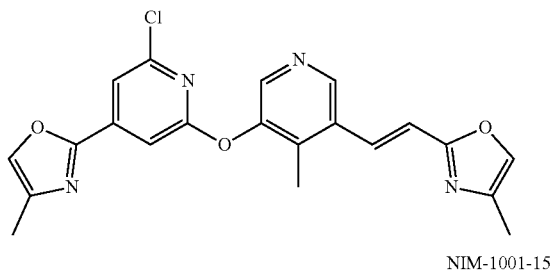
NIM-1001-15
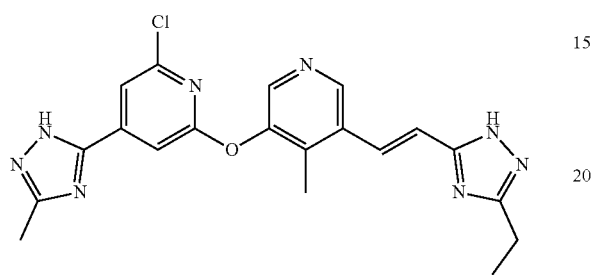
NIM-1001-16
NIM-1001-17
NIM-1001-18
NIM-1001-19
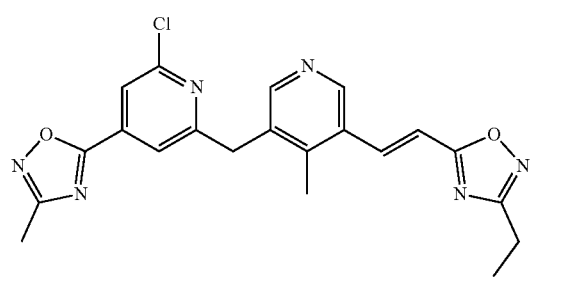
NIM-1001-20
NIM-1001-21
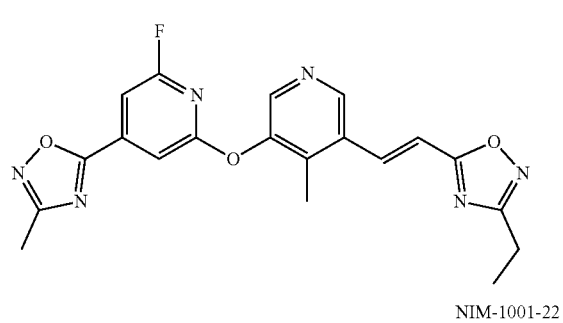
NIM-1001-22
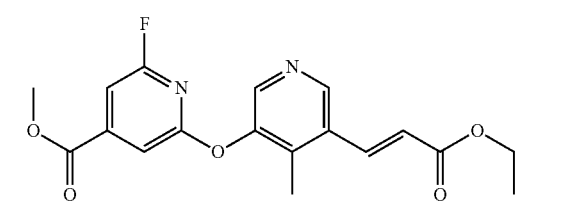
NIM-1001-23
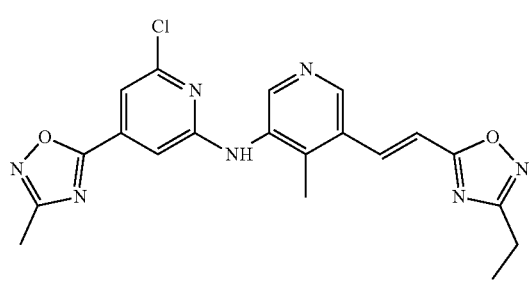
NIM-1001-24
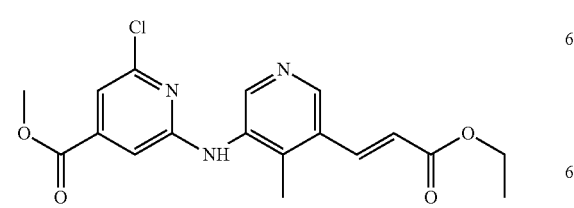
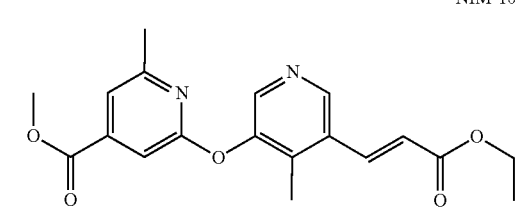

NIM-1001-25
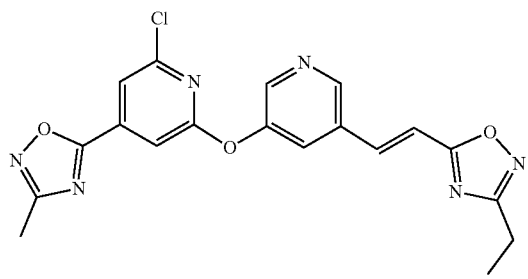
NIM-1001-26
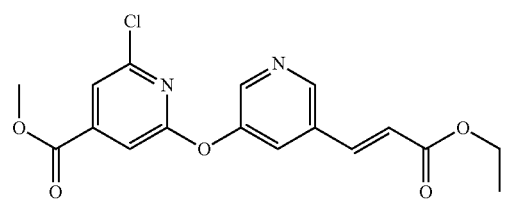
NIM-1001-27
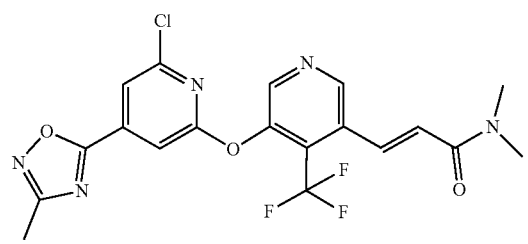
NIM-1001-28
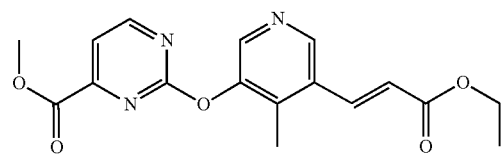
NIM-1001-20
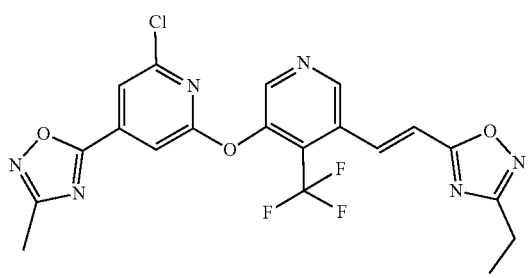
NIM-1001-30
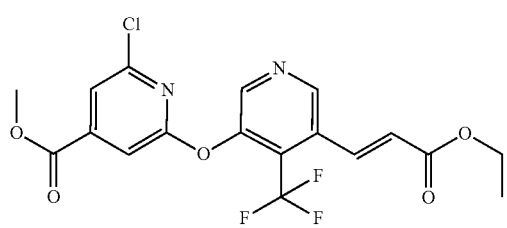
NIM-1001-31
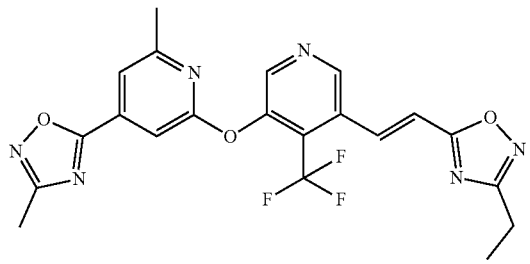
NIM-1001-32
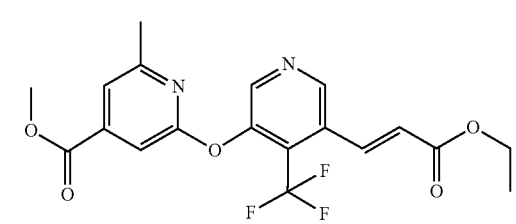
NIM-1001-3
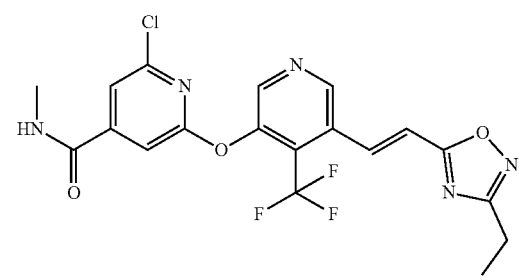
NIM-1001-34
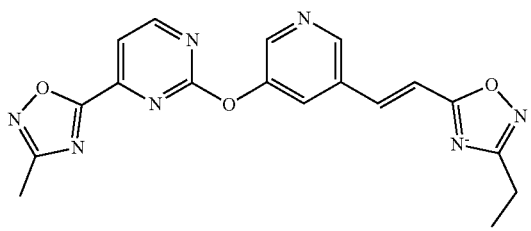
NIM-1001-35
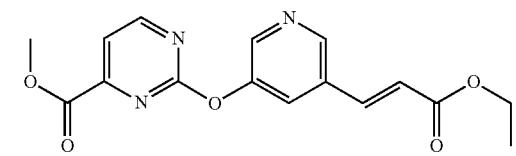
NIM-1001-36

NIM-1001-37

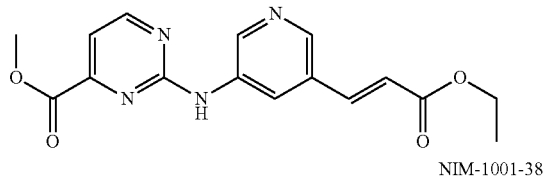

NIM-1001-38

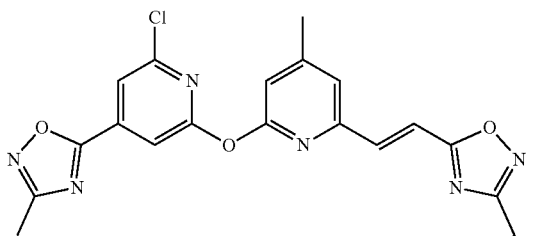

NIM-1001-39

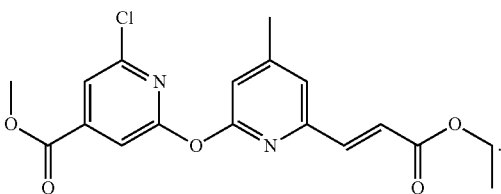

Any of these compounds can be prepared by the skilled artisan without undue experimentation, e.g., by using the methods described in Example 2, or similar methods.

The compound of Formula 1 can be formulated in any compatible excipient, alone or in combination with any other compound, e.g., another pharmaceutically active compound, for example another compound of Formula 1.

Some embodiments of the present invention relate to the use of the above-mentioned compounds comprising Formula 1 formulated in compositions, including pharmaceutical compositions, that comprise at least one of the compounds of the invention in a pharmaceutically acceptable excipient. In some of these embodiments, the compound is suitable for administration to a patient by any parenteral, enteral, transmucosal, or transdermal route which effectively transports the compound of interest to the appropriate or desired site of action, such as oral, nasal, topical, pulmonary, transdermal or parenteral, e. g., rectal, subcutaneous, intravenous, intraurethral, intramuscular, intranasal, ophthalmic solution or an ointment. The preparation of these formulations are within the skill of the art; methods for preparing formulations are provided, for example in Remington's Pharmaceutical Sciences (A.R. Gennaro, Ed.), 20th edition, Williams & Wilkins PA, USA (2000).

In some of these embodiments, the compound is combined with at least another active compound, e.g., another compound effective in preventing or treating a disease, disorder or condition in a mammal. Alternatively or additionally, the compositions can be formulated with at least one inert ingredient as a carrier or excipient such as: cosolvents, surfactants, oils, humectants, emollients, preservatives, stabilizers and antioxidants. Any pharmacologically acceptable buffer may be used, e. g., TRIS or phosphate buffers.

Typical compositions include the compounds of the invention, or derivatives thereof, associated with pharmaceutically acceptable excipients, which may be a carrier or a diluent, by way of example. Such compositions can be in the form of a capsule, sachet, paper or other container. In making the compositions, conventional techniques for the preparation of pharmaceutical compositions may be used. For example, the compound of interest can be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compound of interest can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the active compounds.

For nasal administration, the preparation may contain the compound of interest dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical formulations, the compound of interest is placed in a dermatological vehicle as is known in the art. The amount of the compound of interest to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound of interest and selects the amount of formulation administered, depending upon clinical experience with the patient in question or with similar patients.

For ophthalmic applications, the compound of interest is formulated into solutions, suspensions, and ointments appropriate for use in the eye.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers.

Capsules are prepared by mixing the compound of interest with an inert pharmaceutical diluent and filling the mixture into a hard gelatin capsule of appropriate size. Soft gelatin capsules are prepared by machine encapsulation of slurry of the compound of interest with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e. g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill, such as the use of suitable injectable solutions or suspensions. The formulation, which is sterile, is suitable for various topical or parenteral routes including intra-dermal, intramuscular, intravascular, and subcutaneous.

In addition to the compound of interest, the compositions may include, depending on the formulation and mode of delivery desired, pharmaceutically acceptable, non-toxic carriers or diluents, which include vehicles commonly used to form pharmaceutical compositions for animal or human administration. The diluent is selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, additives can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives, and excipients are those amounts that are effective to obtain a pharmaceutically acceptable formulation in terms of solubility, biological activity, etc.

The compound of interest may be incorporated into a microsphere. The compound of interest can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed and the spheres washed, e. g., with petroleum ether followed by ethanol. Finally, the microspheres can be sieved and collected and dried by filtration.

Starch microspheres can be prepared by adding a warm aqueous starch solution, e. g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air.

The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form Schiff bases with amino groups. Epichlorohydrin activates compounds with nucleophiles such as amino or hydroxyl to an epoxide derivative.

Another embodiment of the invention is the dosage scheme. The term "unit dosage form" refers to physically discrete units suitable as unitary dosages for subjects, e. g., mammalian subjects, e. g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions can be included in kits, which can contain one or more unit dosage forms of the composition and instructions for use to treat one or more of the disorders described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long-term source of therapeutic compound. Such slow-release systems are applicable to formulations for delivery via topical, intraocular, oral, and parenteral routes.

An effective amount of the compound of interest is employed in treatment. The dosage of compounds used in accordance with the invention varies depending on the compound and the disease, disorder or condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient. In general, an effective amount of the compound is that which provides either subjective relief of symptoms or an objectively identifiable improvement as noted by the clinician or other qualified observer. The skilled artisan can determine an appropriate dosage for any particular use of route of administration without undue experimentation.

In some embodiments, the compound is capable of preventing or reducing severity of an inflammatory disease when administered to a mammal with the disease. Any inflammatory disease and be treated with the disease. Non-limiting examples of inflammatory diseases include systemic inflammation, inflammatory bowel disease, a viral infection that causes inflammation, autoimmune encephalomyelitis, multiple sclerosis, systemic lupus erythematosus, Alzheimer's disease, Parkinson's disease, psoriasis, Sjogren's disease, encephalitis, myelitis, meningitis, arachnoiditis, PNS, neuritis, dacryoadenitis, scleritis, episcleritis, keratitis, retinitis, chorioretinitis, blepharitis, conjunctivitis, uveitis, otitis externa, otitis media, labyrinthitis, mastoiditis, carditis, endocarditis, myocarditis, pericarditis, vasculitis, arteritis, phlebitis, capillaritis, sinusitis, rhinitis, pharyngitis, laryngitis, tracheitis, bronchitis, bronchiolitis, pneumonitis, pleuritis, mediastinitis, stomatitis, gingivitis, gingivostomatitis, glossitis, tonsillitis, sialadenitis/parotitis, cheilitis, pulpitis, gnathitis, gastritis, gastroenteritis, enteritis, colitis, enterocolitis, duodenitis, ileitis, caecitis, appendicitis, proctitis, hepatitis, ascending cholangitis, cholecystitis, pancreatitis, peritonitis, dermatitis, folliculitis, cellulitis, hidradenitis, arthritis, dermatomyositis, myositis, synovitis/tenosynovitis, bursitis, enthesitis, fasciitis, capsulitis, epicondylitis, tendinitis, panniculitis, osteochondritis: osteitis/osteomyelitis, spondylitis, periostitis, chondritis, nephritis, glomerulonephritis, pyelonephritis, ureteritis, cystitis, urethritis, oophoritis, salpingitis, endometritis, parametritis, cervicitis, vaginitis, vulvitis, mastitis, orchitis, epididymitis, prostatitis, seminal vesiculitis, balanitis, posthitis, balanoposthitis, chorioamnionitis, funisitis, omphalitis, insulitis, hypophysitis, thyroiditis, parathyroiditis, adrenalitis, lymphangitis and lymphadenitis.

In some embodiments, the inflammatory disease is systemic inflammation, inflammatory bowel disease, a viral infection that causes inflammation, autoimmune encephalomyelitis, multiple sclerosis, systemic lupus erythematosus, Alzheimer's disease, Parkinson's disease, psoriasis, or Sjogren's disease.

In some embodiments where the inflammatory disease is systemic inflammation, administration of the compound to the mammal reduces spleen size in the mammal, reduces the proportion of CD4+ IL21+ cells in the spleen, and/or increases the proportion of CD25+ FOXP3+ cells in the spleen. See, e.g., Example 3 below.

In various embodiments where the inflammatory disease is acute inflammatory bowel disease, and administration of the compound reduces the proportion of CD4+ cells in a colonic lamina propria of the mammal, increases the proportion of CD25+ Treg cells in a colon of the mammal, and/or reduces F4/80hi macrophages in the mammal. See, e.g., Example 4 below.

In certain embodiments where the inflammatory disease is a viral infection that causes inflammation, administration of the compound reduces mortality in a population of mammals infected with the virus, reduces the spread of a non-lethal virus, and/or reduces symptoms from virus infection in a mammal. The virus in these embodiments is any virus now known or later discovered that is capable of infecting mammals. Non-limiting examples of viruses in these embodiments include the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus or a picornavirus such as Coxsackievirus B3 (CVB3). Other viruses include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, adenovirus, human herpesvirus, type 8, human papillomavirus, BK virus, JC virus, smallpox, hepatitis B virus, human bocavirus, parvovirus B19, human astrovirus, Norwalk virus, coxsackievirus, hepatitis A virus, poliovirus, rhinovirus, severe acute respiratory syndrome (SARS) virus, hepatitis C virus, yellow fever virus, dengue virus, West Nile virus, Rubella virus, Hepatitis E virus, and Human immunodeficiency virus (HIV). In some cases, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, hepadnavirus hepatitis B virus (HBV), woodchuck hepatitis virus, ground squirrel (Hepadnaviridae) hepatitis virus, duck hepatitis B virus, heron hepatitis B virus, herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma-associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, yabapox virus, flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Filovirus Ebola virus, Marburg virus, metapneumoviruses (MPV) such as human metapneumovirus (HMPV), rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is influenza A virus, e.g., strain H1N1. See, e.g., Example 5 below.

In some embodiments where the inflammatory disease is autoimmune encephalomyelitis or multiple sclerosis, administration of the compound reduces the proportion of CD4+ IL17+ T cells in the spinal cord of the mammal, reduces astrocytes or activated glia in the spinal cord of the mammal, and/or reduces GFAP positive staining in the spinal cord of the mammal. See, e.g., Example 6 below.

In various embodiments the inflammatory disease is systemic lupus erythematosus, lupus nephritis, cutaneous lupus or lupus with central nervous system (CNS) involvement, the compound reduces urine protein levels in the mammal, increases splenic CD25+ FOXP3+ regulatory T cells in the mammal, and/or decreases splenic CD4+ IL17+ cells in the mammal. See, e.g., Example 7 below.

In certain embodiments where the inflammatory disease is Alzheimer's disease, administration of the compound decreases the anxiety response by the mammal, decreases neutrophils in the mammal, and/or decreases CD4+ 17+ cells in the mammal. See, e.g., Example 8 below.

In some embodiments where the inflammatory disease is Parkinson's disease, administration of the compound improves gait by the mammal, decreases splenic CD4+ IL21+ cells in the mammal, and/or decreases splenic CD4+ IL17+ cells in the mammal. See, e.g., Example 9 below.

In various embodiments where the inflammatory disease is psoriasis, administration of the compound decreases splenic CD4+ TNF+ T cells in the mammal, decreases splenic CD4+ IL17+ in the mammal, and/or decreases inflammatory macrophages in the mammal. See, e.g., Example 10 below.

In certain embodiments where the inflammatory disease is Sjogren's syndrome, administration of the compound decreases diseases disease severity and tissue pathology of lacrimal and/or salivary glands in the mammal. See, e.g., Example 11 below.

The pharmaceutical compositions described above can be formulated for administration to any mammal, including but not limited to farm animals (e.g., cows, pigs, goats, sheep, llamas, alpacas, mink, etc.) and domestic animals, (e.g., dogs, cats, mice, rats, gerbils, guinea pigs, ferrets, etc) and humans.

Also provided herein are methods of treating mammals using the pharmaceutical compositions of Formula 1 described above.

Thus, in some embodiments, a method of treating a mammal undergoing an inflammatory disease is provided. The method comprises administering the above-identified compound to the mammal in a manner sufficient to reduce the severity of the systemic inflammation. In some embodiments, the inflammatory disease is systemic inflammation, inflammatory bowel disease, a viral infection that causes inflammation, autoimmune encephalomyelitis, multiple sclerosis, systemic lupus erythematosus, Alzheimer's disease, Parkinson's disease, psoriasis, or Sjogren's disease, as discussed above.

These methods can be used to treat any mammal, including but not limited to farm animals (e.g., cows, pigs, goats, sheep, llamas, alpacas, mink, etc.) and domestic animals, (e.g., dogs, cats, mice, rats, gerbils, guinea pigs, ferrets, etc) and humans. Additionally these methods can utilize any form of administration, including any parenteral, enteral, transmucosal, or transdermal administration, as discussed above.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Molecular Docking of NIM-1001 Compounds

Methods

A grid space was defined. Three dimensional structures of ligands with defined atomic charge were docked into the defined region. A binding affinity was calculated based on interactions between the ligand and protein structure. Potential ligands were analyzed and ranked by raw binding affinity, molecular weight normalized binding affinity, and binding pose among other criteria.

Results

Thirty-nine exemplary docked structures, designated NIM-1001-1 to NIM-1001-39, and resultant binding affinities are presented in FIGS. 1A-1H. Docked structures were identified to have binding affinities ranging from −7.4 kcal/mol to −9.4 kcal/mol. Structures with the most favorable binding affinity included NIM-1001-2, NIM-1001-27, and NIM-1001-33; all of which had binding affinities of magnitude greater than 9.

Example 2. Synthesis of NIM-1001-8

The synthesis of methyl (E)-2-chloro-6-((5-(3-ethoxy-3-oxoprop-1-en-1-yl)-4-methylpyridin-3-yl)oxy)isonicotinate (NIM-1001-8) was a four step process.

Hydrobromic acid was added to a solution of 3-bromo-5-methoxy-4-methylpyridine in acetic acid. Mixture was stirred for 3 days at 120° C. with addition of HBr every 24 h. After completion of reaction, the reaction mixture was neutralized with NaOH and extracted with ethyl acetate. Product was isolated as 5-bromo-4-methylpyridin-3-ol.

Cesium carbonate and methyl 2,6-dichloropyridine-4-carboxylate were added to a solution of 5-bromo-4-methylpyridin-3-ol in DMF and stirred at 120° C. for 4 h. After completion of reaction, reaction mixture was filtered through celite bed. Filtrate was evaporated under reduced pressure to get crude, which was taken forward to next step without purification.

Concentrated sulfuric acid was added to a solution of crude product in methanol and stirred at 70° C. for 16 h. After completion of reaction, solvent was evaporated under reduced pressure and extracted with ethyl acetate. Crude product was isolated and purified to obtain methyl (E)-2-chloro-6-((5-bromo-4-methylpyridin-3-yl)oxy)isonicotinate.

Triethylamine, ethyl acrylate, and tris(o-tolyl)phosphine was added to the methyl (E)-2-chloro-6-((5-bromo-4-methylpyridin-3-yl)oxy)isonicotinate in acetonitrile. It was stirred under nitrogen atmosphere for 10 min, then palladium (II) acetate was added and stirred at 90° C. for 18 h. After completion of reaction, solvent was evaporated under reduced pressure to get crude. The crude was subjected to purification to get desired product NIM-1001-8 as solid. $^1$H NMR (400 MHz, DMSO-d6): δ 8.83 (s, 1H), 8.46 (s, 1H), 7.83 (d, J=16.00 Hz, 1H), 7.62 (s, 1H), 7.53 (s, 1H), 6.75 (d, J=16.00 Hz, 1H), 4.23 (q, J=7.20 Hz, 2H), 3.92 (s, 3H), 2.22 (s, 3H), 1.28 (t, J=6.80 Hz, 3H).

Example 3. Use of NIM-1001 Compounds in a Mouse Model of Systemic Inflammation

Introduction

Systemic inflammation can result from infectious disease, loss of self-tolerance and other unresolved perturbations to the immune system. The bm12 model is induced by the transfer of lymphocytes from bm12 mice to C57BL/6 mice. Due to a mismatch in the MHCII amino acid sequence, antigen presenting cells in the recipient mice induce alloactivation of donor lymphocytes. This alloactivation leads to prominent expansion of donor T follicular helper cells and recipient GC B and plasma cells. This adoptive transfer model has been used as a model of graft-versus-host disease and also shares immunological changes with SLE-like disease, presenting with antinuclear antibodies, IgG deposits in the kidneys and type I IFN production.

Methods

Mouse model. Wild-type (WT) were used on a C57BL/6 background. Bm12 mice were used on a C57BL/6 background with a mutation in the MHCII allele. Spleens and major lymph nodes were collected from bm12 mice into RPMI and crushed to provide cellular suspensions. Red blood cells were lysed. Cells were counted and resuspended into sterile PBS. $2.5 \times 10^7$ cells/mouse were injected intraperitoneally into WT recipients on day 0 of the project. Treatments, or vehicle control, were administered by orogastric gavage daily, beginning one week after transfer, in a 0.5% methylcellulose suspension to provide 20 mg/kg/day.

Immunological analysis. Spleens were excised, weighed, crushed and filtered to provide a cellular suspension. Red blood cells were lysed. Cells were labeled with mixtures of extracellular (CD45, CD3, CD4, CD8, CD25) and intracellular (FOXP3, IL21, IL10) antibodies in a sequential live staining in 96-well plates in preparation for flow cytometry. Data was captured on a BD FACS Celesta and analyzed using FacsDiva.

Results

Figure 2A:
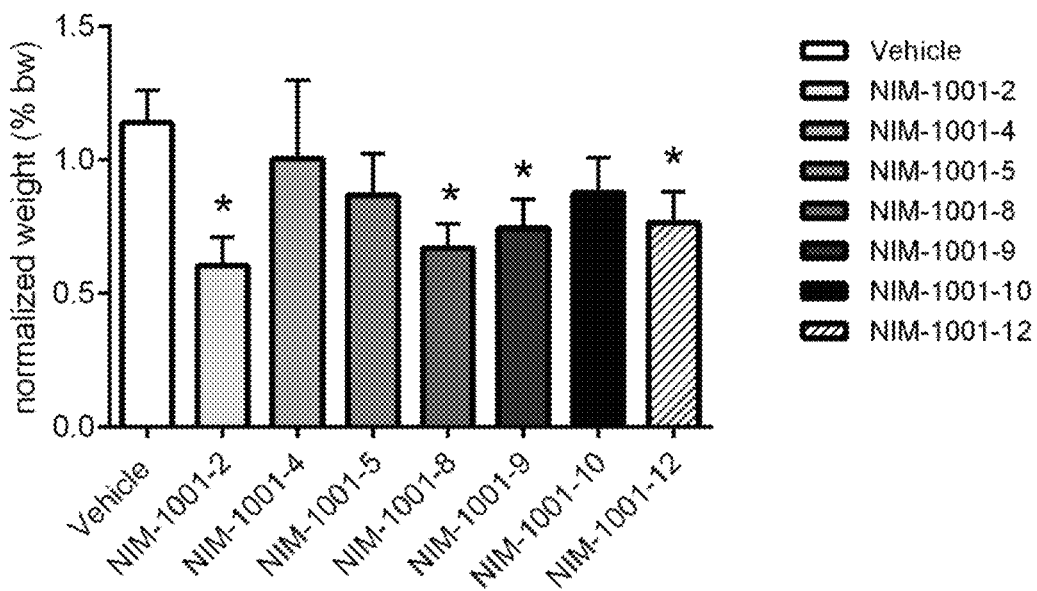
FIG. 2A is a graph showing reductions in spleen size after treatment of a mouse model of systemic inflammation with various compounds of Formula 1.
Figure 2B:
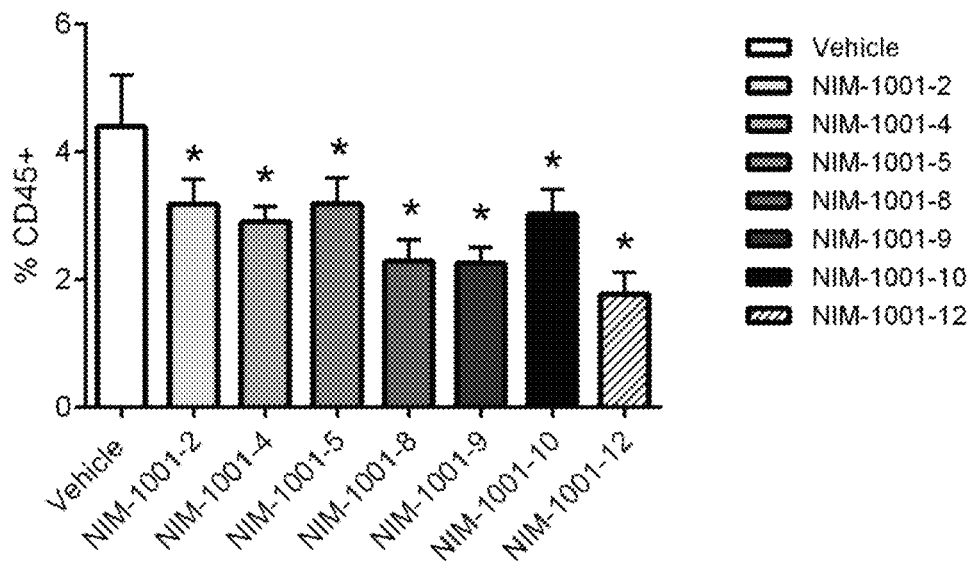
FIG. 2B is a graph showing reductions in CD4+ IL21+ cells after treatment a mouse model of systemic inflammation with various compounds of Formula 1.
Figure 2C:
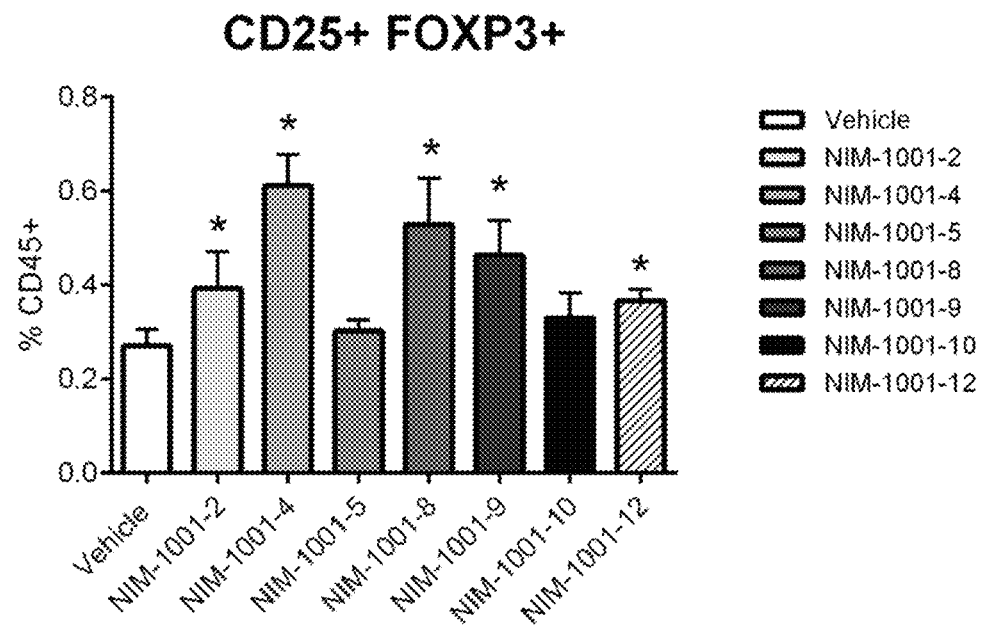
FIG. 2C is a graph showing increases in CD25+ FOXP3+ cells after treatment of a mouse model of systemic inflammation with various compounds of Formula 1.

Oral treatment with NIM-1001-2, NIM-1001-8, NIM-1001-9 and NIM-1001-12 significantly reduced spleen size in proportion to overall body weight (FIG. 2A). NIM-1001-4, NIM-1001-5, and NIM-1001-10 reduced the normalized spleen size at a lesser degree relative to the vehicle treated group. All tested treatments reduced the proportion of CD4+ IL21+ cells in the spleen relative to vehicle (FIG. 2B). NIM-1001-2, NIM-1001-4, NIM-1001-8, NIM-1001-9 and NIM-1001-12 significantly increased the proportion of CD25+ FOXP3+ regulatory T cells in the spleen relative to vehicle (FIG. 2C). NIM-1001-4 and NIM-1001-8 induced the largest magnitude of increase across the tested treatments.

Example 4. Use of NIM-1001 Compounds in an Model of Acute Inflammatory Bowel Disease Introduction Inflammatory bowel disease is a multifactorial disease that involves dysfunction of the epithelial barrier, perturbed interactions with the microbiome and persistent inflammation of the intestinal mucosa. The dextran sulfate sodium (DSS) model provides a model system where the epithelial barrier is disrupted in the distal gastrointestinal allowing for translocation of bacteria and generation of immune responses.

Methods

DSS model. Mice were given DSS in drinking water for seven days. At project initiation, mice were 8 weeks of age and began dosing 24 hours after being placed on DSS. Mice were weighed and scored daily for symptoms of disease (diarrhea, rectal bleeding, rectal inflammation, overall behavior). Treatments were prepared within a 0.5% methylcellulose (12-15 cP) solution. The dosage used was 10 mg/kg delivered once daily.

Flow Cytometry. Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD25, F4/80, CD11b, MHCII) antibodies in a sequential live staining in 96-well plates. Data was acquired using a FACS Celesta flow cytometer with FACSDiva software.

Results

Figure 3A:
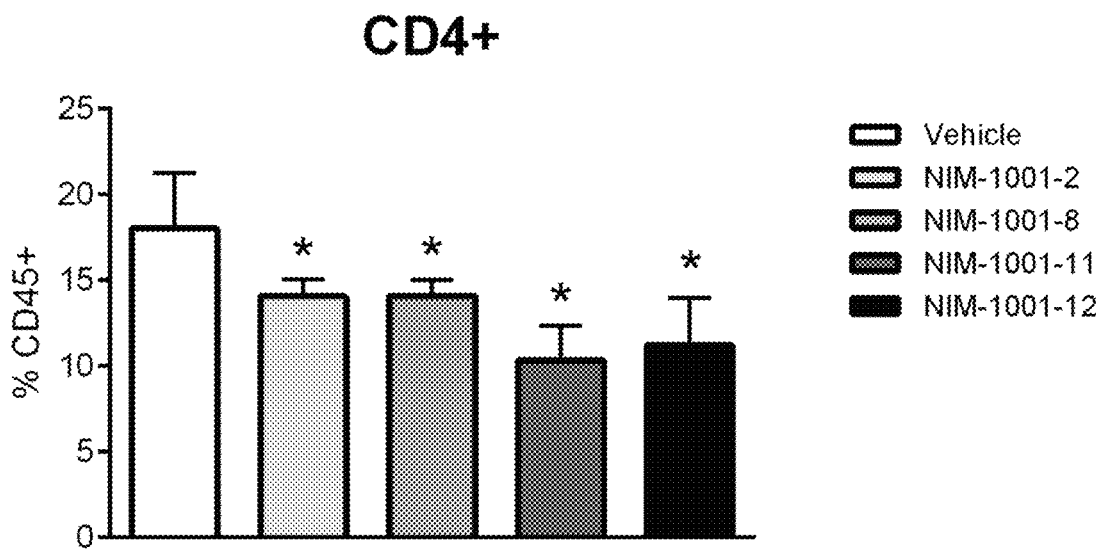
FIG. 3A is a graph showing reductions in CD4+ cells after treatment of a mouse model of acute inflammatory bowel disease with various compounds of Formula 1.
Figure 3B:
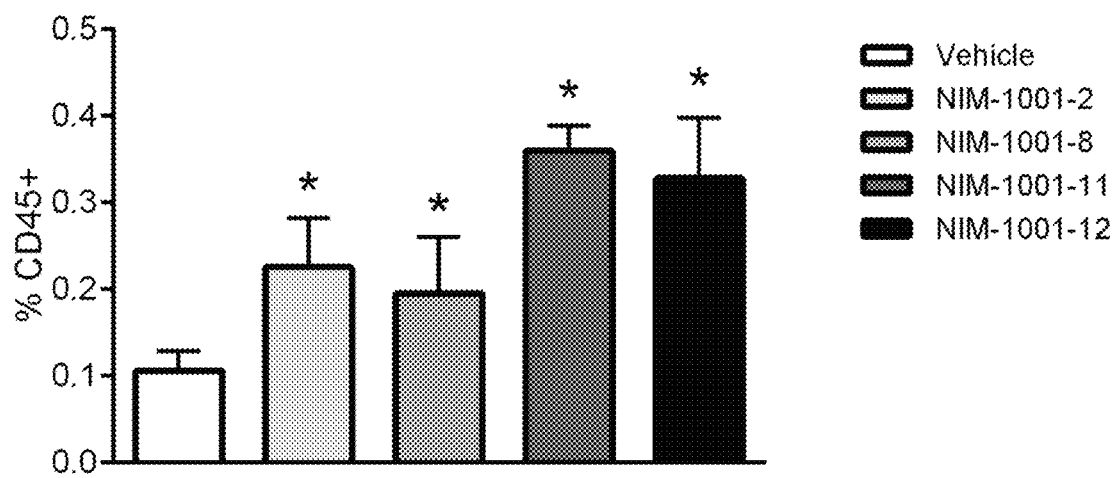
FIG. 3B is a graph showing increases in CD25+ Treg cells after treatment of a mouse model of acute inflammatory bowel disease with various compounds of Formula 1.
Figure 3C:
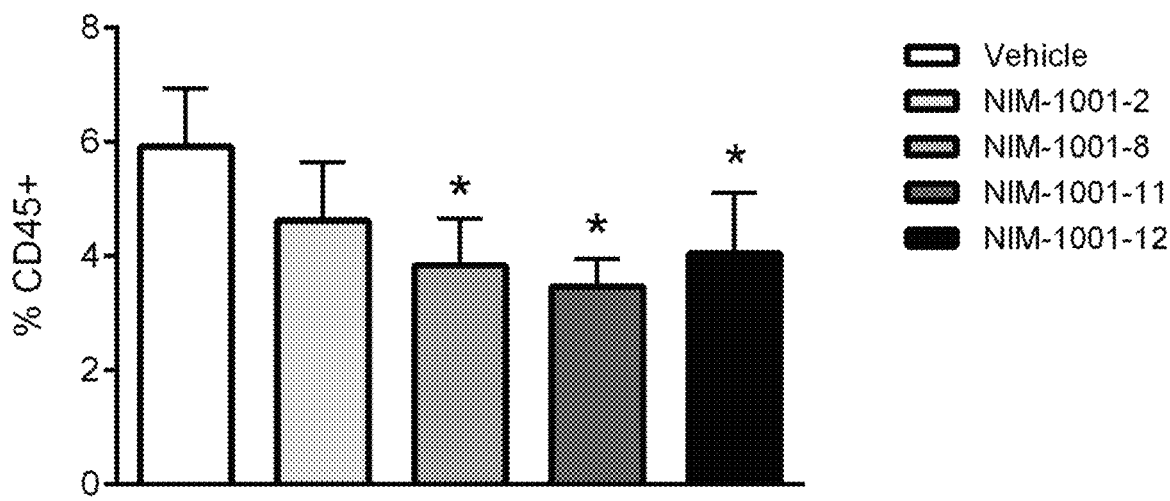
FIG. 3C is a graph showing reductions in F4/80hi cells after treatment of a mouse model of acute inflammatory bowel disease with various compounds of Formula 1.

Oral treatment with NIM-1001-2, NIM-1001-8, NIM-1001-11, and NIM-1001-12 reduced the proportion of CD4+ T cells in the colonic lamina propria relative to the vehicle treated group (FIG. 3A). Each NIM-1001 compound tested also significantly increased the proportion of CD25+ Tregs in the colon relative to vehicle (FIG. 3B). Each NIM-1001 compound reduced F4/80hi macrophages relative to vehicle with significant reductions induced by NIM-1001-8, NIM-1001-11, and NIM-1001-12 (FIG. 3C).

Example 5. Use of NIM-1001 Compounds in a Model Viral Infection

Introduction

Viral infections remain a primary concern in global public health. In particular, respiratory viral infections are common causes of global pandemics with rapid emergence that results in a lack of first-line treatment options. Commonly, after the replication phase which ends a few days after exposure, the primary driver of tissue damage, morbidity and mortality is unresolved immune response. As a result, host-targeted therapies may serve as valuable tools to combat emergent viral threats.

Methods

Wild type C57BL/6 mice were anesthetized by isoflurane inhalation. Mice were infected with influenza A (H1N1) intranasally at a challenge titer of $2 \times 10^4$ TCID50/mL. Mice were treated daily with NIM-1001-2, NIM-1001-8, or NIM-1001-9 at a dose of 25 mg/kg orally via gavage. Mice were monitored daily.

Results

Figure 4:
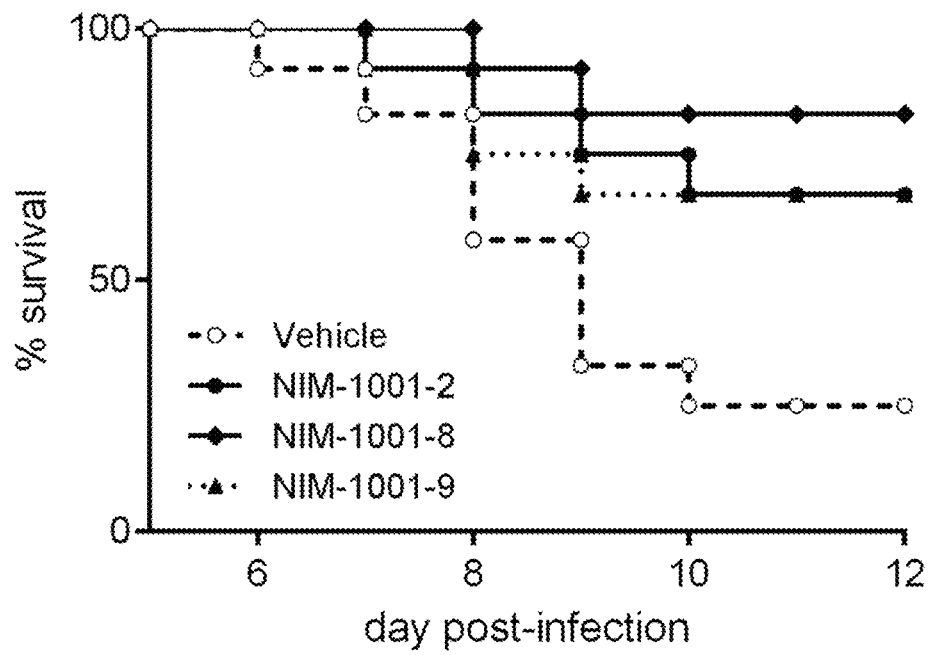
FIG. 4 is a graph showing increases in % survival after treatment of mice infected with influenza A H1N1 with various compounds of Formula 1.

Results are shown in FIG. 4. Vehicle treatment resulted in mortality beginning at day 6 and reaching 25% survival by day 10. Oral treatment with NIM-1001-2 and NIM-1001-9 delayed first mortality by one day and resulted in survival of two-thirds of each group at day 10. Oral treatment with NIM-1001-8 delayed first mortality by two days and resulted in 83% survival at day 10.

Example 6. Use of NIM-1001-8 in a Model of Experimental Autoimmune Encephalomyelitis Introduction Multiple sclerosis is an inflammatory disease where the immune system reacts to the central nervous system resulting in relapsing and remitting or progressive damage. This neurological damage results in impaired motor control, disability, vision loss, depression, and pain among other symptoms. A common immunological event in many patients with MS is an increase in number or activity of Th17 cells, especially within relapsing and remitting forms of disease. Meanwhile, overactivation of microglia contributes to neurological damage.

Methods

Mouse model. C57BL6 mice were challenged at 10- to 16-weeks of age with MOG immunization with complete Freund's adjuvant. MOG emulsion was administered to the cervical region and the hind flank at 100 μL per site to each mouse. After 10 days, spleens were harvested. Isolated splenocytes were cultured in the presence of MOG, IL-12 and anti-interferon gamma for 3 days. Splenocytes were then washed and injected into recipient mice at approximately 20 million cells per mouse. Oral treatment with NIM-1001-8 (20 mg/kg) or vehicle was initiated at 7 days post-transfer. Mice were be scored (0-3) daily for disease activity (coordination, gait, paralysis).

Flow Cytometry. Spinal cords were excised and digested with papain and DNase. Immune cells were purified by Percoll gradient. Cells were labeled with mixtures of extracellular (CD45, CD3, CD4, CD8, CD25) and intracellular (IL17) antibodies in a sequential live staining in 96-well plates in preparation for flow cytometry. Data was captured on a BD FACS Celesta and analyzed using FacsDiva.

Figure 5A:
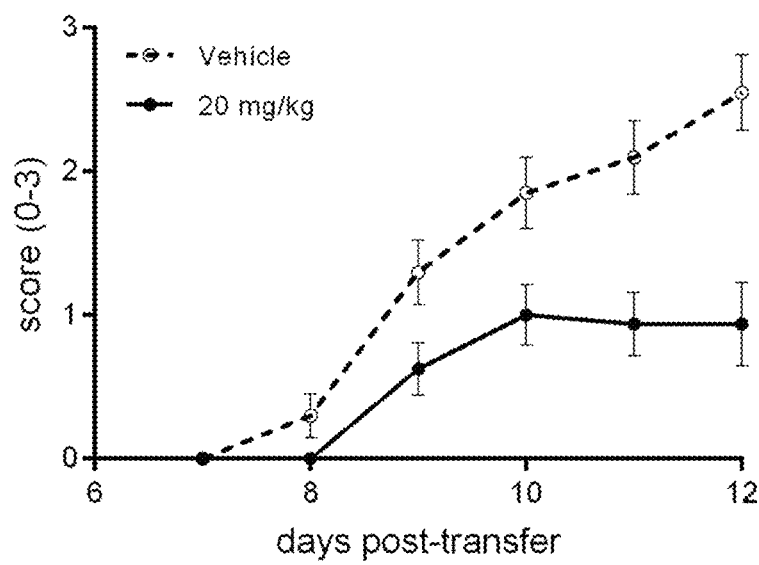
FIG. 5A is a graph showing a reduction in disease severity after treatment of a mouse model of experimental autoimmune encephalomyelitis and multiple sclerosis with NIM-1001-8.
Figure 5B:
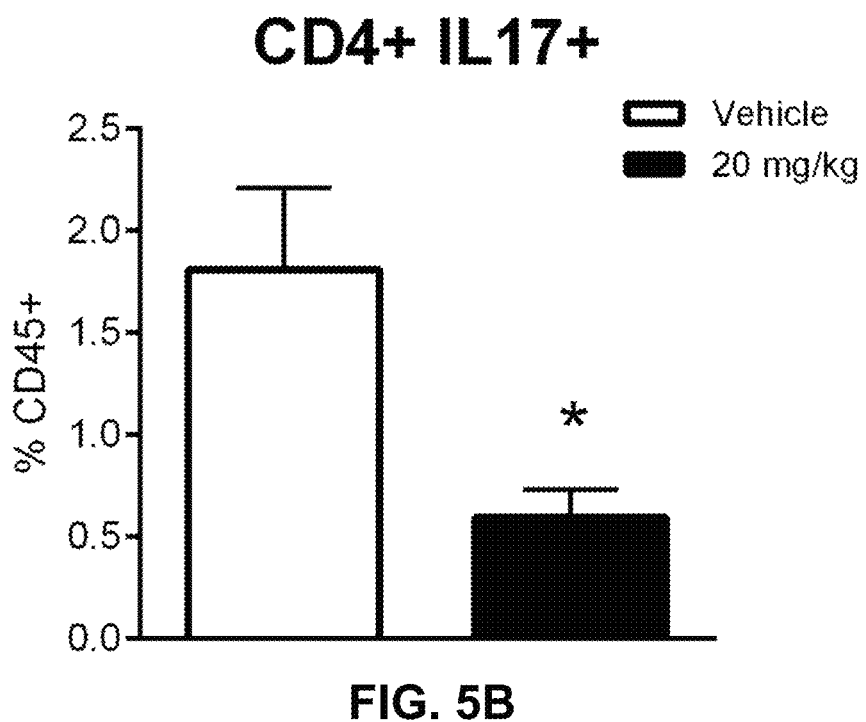
FIG. 5B is a graph showing a reduction CD4+ IL17+ cells after treatment of a mouse model of experimental autoimmune encephalomyelitis and multiple sclerosis with NIM-1001-8.
Figure 5C:
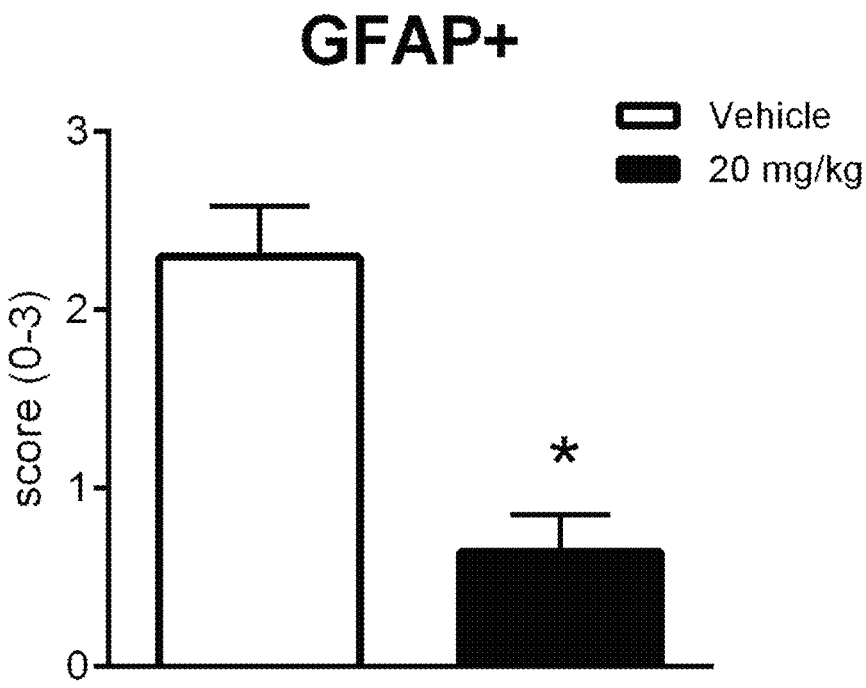
FIG. 5C is a graph showing a reduction GFAP+ staining cells after treatment of a mouse model of experimental autoimmune encephalomyelitis and multiple sclerosis with NIM-1001-8.

Histology. Sections of the spinal cord from the lumbar region were extracted and fixed in formalin. Samples were embedded in paraffin and sectioned. By immunohistochemistry, samples were stained for the presence of glial fibrillary acidic protein (GFAP). Slides were assessed microscopically and scored (0-3) for the intensity and frequency of GFAP positive cells. GFAP is a common protein marker for astrocytes in the central nervous system Results Oral NIM-1001-8 resulted in an amelioration of overall disease severity throughout the course of the experiment (FIG. 5A). NIM-1001-8 decreased the proportion of CD4+ IL17+ T cells in the spinal cord (FIG. 5B) and the presence of GFAP positive staining in the spinal cord (FIG. 5C).

Example 7. Use of NIM-1001-8 in a Genetic Mouse Model of SLE

Introduction

Systemic lupus erythematosus (SLE) is a systemic autoimmune disease that can cause damage to kidneys, cardiovasculature, and joints. SLE is a result of a complex interaction of genetic factors that results in immunological disease manifested primarily through a generation of autoantibodies. The MRL/lpr model is a spontaneous genetic model induced by polymorphisms in Fas/FasL. Due to these mutations, MRL/lpr mice exhibit increased lymphoproliferation, splenomegaly, glomerulonephritis, and enlarged lymph nodes. The MRL/lpr model remains an important preclinical model due to the prevalence of Fas/FasL polymorphisms in SLE-susceptible individuals and the presence of double-negative T cells in human SLE.

Methods

Mouse model. Female MRL/lpr mice were obtained at 8 weeks of age. Mice were followed for four weeks for the development of proteinuria. Mice possessing proteinuria scores≥2 were randomized into the project at 12 weeks of age. Treatment with NIM-1001-8, or vehicle control, were administered by orogastric gavage daily, beginning at 12 weeks of age, in a 0.5% methylcellulose suspension.

Immunological analysis. Urine was collected for assay for protein content to test for kidney function. Spleens were excised, crushed and filtered to provide a cellular suspension. Red blood cells were lysed. Cells were labeled with mixtures of extracellular (CD45, CD3, CD4, CD8, CD25) and intracellular (FOXP3, IL17) antibodies in a sequential live staining in 96-well plates in preparation for flow cytometry. Data was captured on a BD FACS Celesta and analyzed using FacsDiva.

Results

Figure 6A:
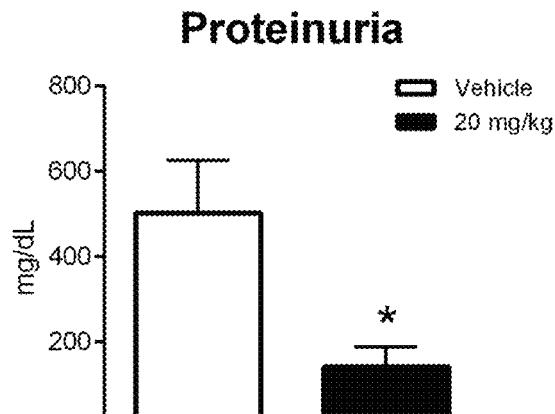
FIG. 6A is a graph showing a reduction of urine protein levels after treatment of a mouse model of systemic lupus erythematosus with NIM-1001-8.
Figure 6B:
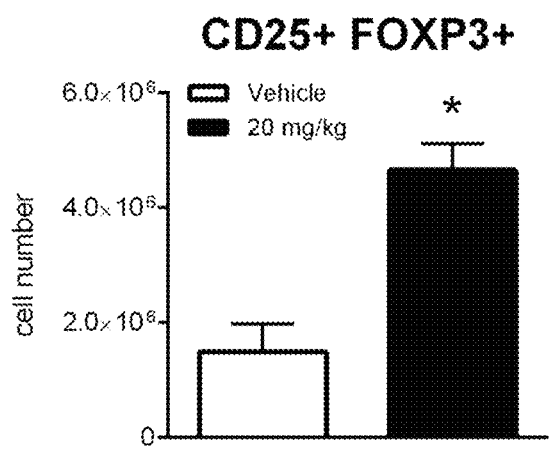
FIG. 6B is a graph showing an increase in splenic CD25+ FOXP3+ regulatory T cells after treatment of a mouse model of systemic lupus erythematosus with NIM-1001-8.
Figure 6C:
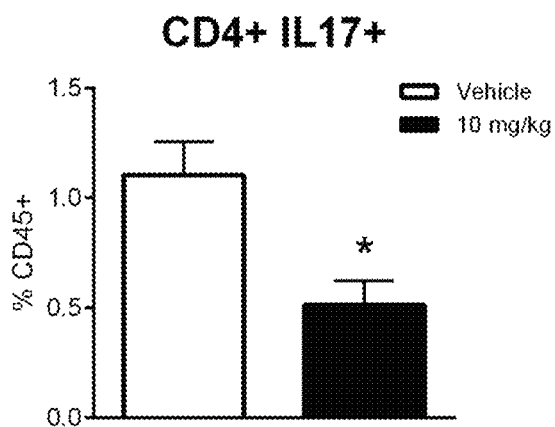
FIG. 6C is a graph showing a decrease in splenic CD4+ IL17+ cells after treatment of a mouse model of systemic lupus erythematosus with NIM-1001-8.

Urine protein levels were reduced more than two-fold with NIM-1001-8 treatment relative to vehicle (FIG. 6A). NIM-1001-8 treatment resulted in a significant increase in CD25+ FOXP3+ regulatory T cells (FIG. 6B) and a significant decrease in CD4+ IL17+ cells (FIG. 6C). Statistical significance ($P<0.05$) is marked by asterisks.

Example 8. Use of NIM-1001-8 in a Genetic Model of Alzheimer's Disease

Introduction

Alzheimer's disease is one of the most common neurodegenerative diseases resulting in memory loss and reduction of overall cognitive abilities. The pathogenesis of disease involves immune, metabolic and neurologic factors resulting in the generation of amyloid beta deposits or plaques and tau tangles. Numerous mouse models exist that spontaneously generate similar neurological pathology and cognitive impairment.

Methods

Mouse model. Genetically modified mice that spontaneously develop cognitive impairment at 4 months of age and histological signs of disease at 6 months of age were randomized into the project at 24 weeks of age. Mice were orally treated with vehicle or NIM-1001-8 (10 mg/kg) for eight weeks. After eight weeks of treatment, mice were evaluated using a light-dark test to measure the time spent in the light relative to the dark. This is a measure of an anxiety response. Genetically modified mice were compared to age-matched wild-type mice (negative control).

Flow Cytometry. Brains were collected into RPMI/FBS buffer containing collagenase (300 U/mL) and DNase (50 U/mL) for digestion. Tissues were digested for 30 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched immune cell fractions. Cells were labeled with mixtures of extracellular (CD45, CD3, CD4, CD8, CD11b, Gr1) and intracellular (IL17) antibodies in a sequential live staining in 96-well plates. Data was acquired using a FACS Celesta flow cytometer with FACSDiva software.

Results

Figure 7A:
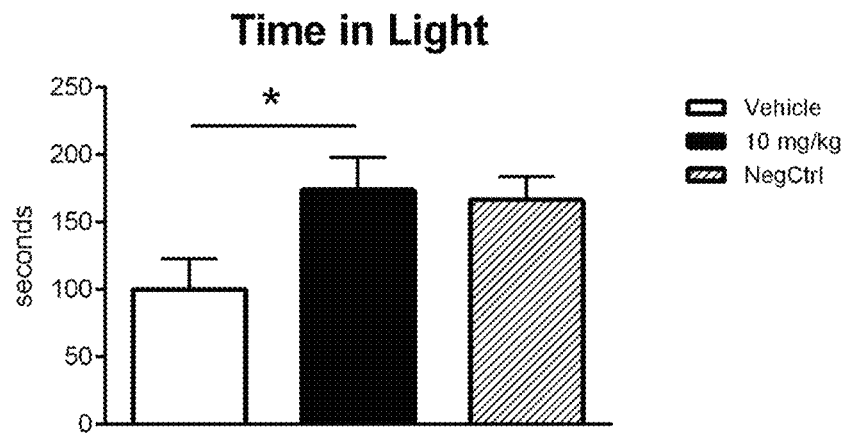
FIG. 7A is a graph showing an increase in time spent in the light after treatment of a mouse model of Alzheimer's disease with NIM-1001-8.
Figure 7B:
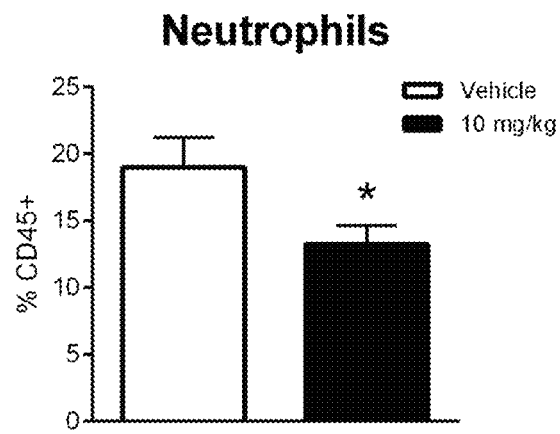
FIG. 7B is a graph showing a decrease in neutrophils after treatment of a mouse model of Alzheimer's disease with NIM-1001-8.
Figure 7C:
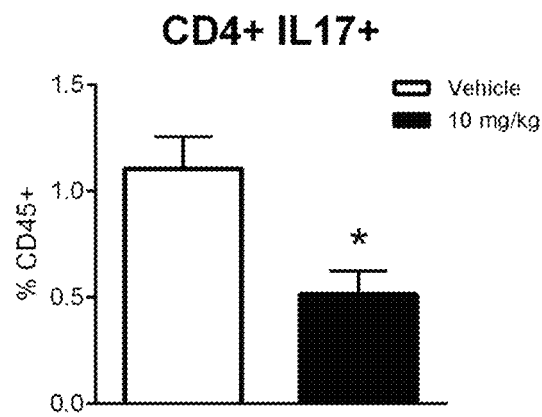
FIG. 7C is a graph showing a decrease in CD4+ IL17+ cells after treatment of a mouse model of Alzheimer's disease with NIM-1001-8.

Oral NIM-1001-8 treatment significantly increased time spent in the light relative to vehicle and restored the time to equal that of the negative control group (FIG. 7A). Immunologically, NIM-1001-8 decreased the proportions of neutrophils (FIG. 7B) and CD4+ IL17+ T cells (FIG. 7C) in the brain relative to vehicle. Statistical significance (P<0.05) is marked by asterisks.

Example 9. Use of NIM-1001-8 in a Mouse Model of Parkinson's Disease

Introduction

Parkinson's disease is a common neurodegenerative condition that causes tremors and deficits in motor control. The disease results from damage to dopaminergic neurons, particularly in the midbrain. Mouse models of the disease exist that cause damage to these same neurons through the administration of various chemicals.

Methods

Mouse model. Mice were administered intraperitoneal injections of 1-methyl-4-phenyl-1,2,3,6-tetrahydropyridine (MPTP) and probenecid three times weekly for 4 weeks. In the second week of injections, oral treatment with vehicle or NIM-1001-8 (25 mg/kg) was initiated once daily. After four weeks of injections, motor control was assessed by counting the number of step errors during a challenging beam test. Mice challenged with MPTP were compared to mice challenged with a sham injection (negative control).

Flow Cytometry. Spleens were excised, crushed and filtered to provide a cellular suspension. Red blood cells were lysed. Cells were labeled with mixtures of extracellular (CD45, CD3, CD4, CD8, CD25) and intracellular (IL21, IL17) antibodies in a sequential live staining in 96-well plates in preparation for flow cytometry. Data was captured on a BD FACS Celesta and analyzed using FacsDiva.

Results

Figure 8A:
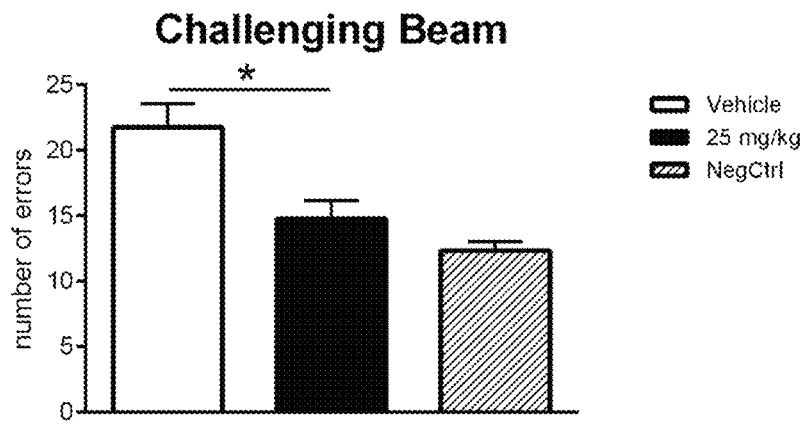
FIG. 8A is a graph showing a decrease in step errors during a challenging beam test after treatment of a 1-methyl-4-phenyl-1,2,3,6-tetrahydropyridine induced model of Parkinson's disease with NIM-1001-8.
Figure 8B:
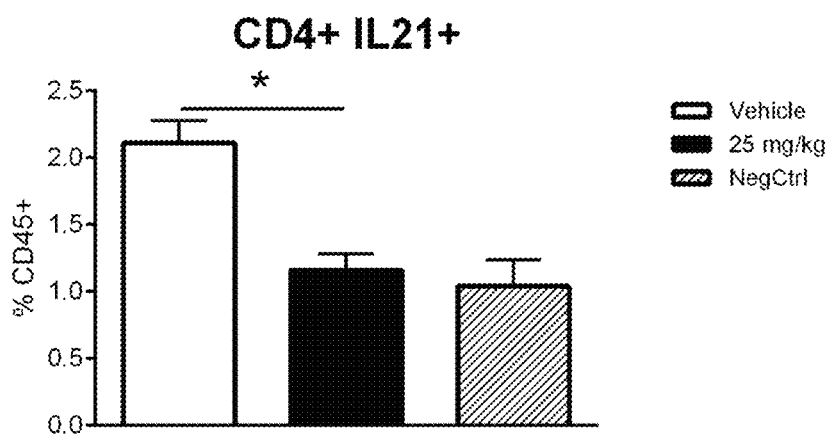
FIG. 8B is a graph showing a decrease in splenic CD4+ IL21+ T cells after treatment of a 1-methyl-4-phenyl-1,2,3,6-tetrahydropyridine induced model of Parkinson's disease with NIM-1001-8.
Figure 8C:
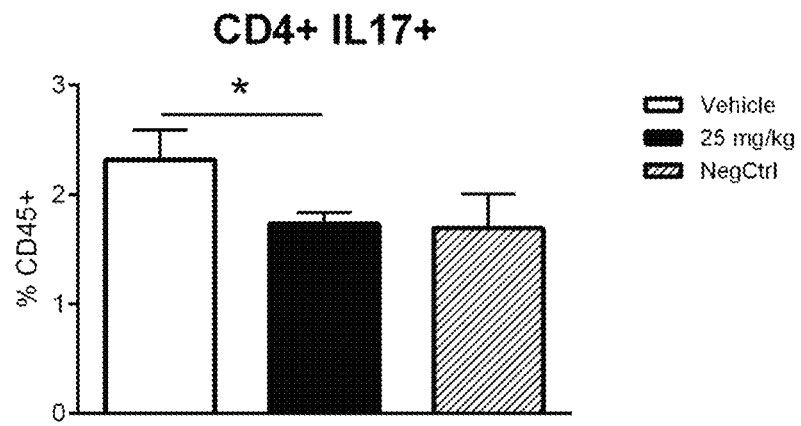
FIG. 8C is a graph showing a decrease in splenic CD4+ IL17+ T cells after treatment of a 1-methyl-4-phenyl-1,2,3,6-tetrahydropyridine induced model of Parkinson's disease with NIM-1001-8.

Oral NIM-1001-8 significantly reduced the number of step errors during a challenging beam test relative to vehicle treated mice with near complete abrogation of MPTP effects when compared to negative controls (FIG. 8A). NIM-1001-8 also reduced systemic inflammation with significant reductions of CD4+ IL21+ (FIG. 8B) and CD4+ IL17+ (FIG. 8C) T cells within the spleen. Statistical significance (P<0.05) is marked by asterisks.

Example 10. Use of NIM-1001-8 in a Model of Psoriasis

Introduction

Psoriasis (PsO) is a common dermatological condition in which the increased immune system activation occurs in the skin. PsO can results in the formation of plaques and thickened regions of the skin, itchiness, and general discomfort. Immunologically, PsO is commonly thought to be driven by Th17 cells with IL-17/IL-23 treatments providing some degree of therapeutic benefit.

Methods

IMQ-induced model. C57BL/6 mice were anesthetized, shaved, and briefly exposed to depilatory cream on the surface of the back. Mice were given three days to recover from the procedure prior to entry to the study. After 3 days, mice were challenged with approximately 60 mg of 0.5% imiquimod cream daily by spreading cream over the shaved area. Oral treatment with vehicle or NIM-1001-8 (20 mg/kg) occurred daily.

Analysis. Spleens were excised and crushed by microscope slides. Red blood cells were hypotonically lysed from the resultant suspension. Samples were filtered, washed and centrifuged prior to staining. Cells were labeled with mixtures of extracellular (CD45, CD3, CD4, CD8, CD25, F4/80, CD11b, MHCII) and intracellular (TNF, IL17) antibodies in a sequential live staining in 96-well plates in preparation for flow cytometry. Data was captured on a BD FACS Celesta and analyzed using FacsDiva.

Results

Figure 9A:
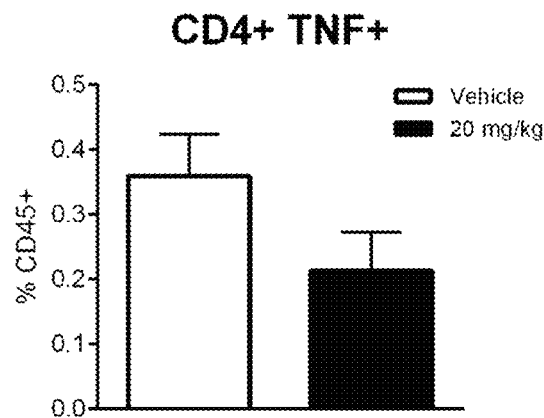
FIG. 9A is a graph showing a decrease in splenic CD4+ TNF+ T cells after treatment of an imiquimod induced model of psoriasis with NIM-1001-8.
Figure 9B:
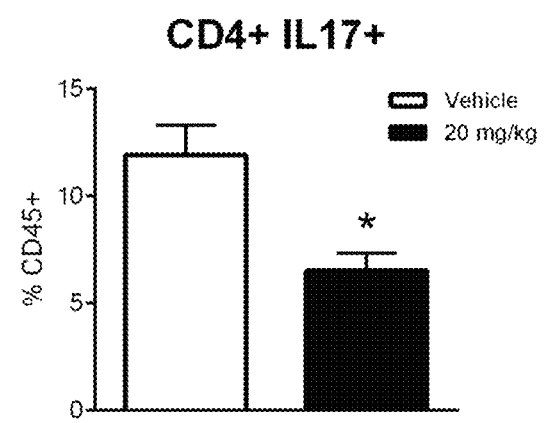
FIG. 9B is a graph showing a decrease in splenic CD4+ IL17+ cells after treatment of an imiquimod induced model of psoriasis with NIM-1001-8.
Figure 9C:
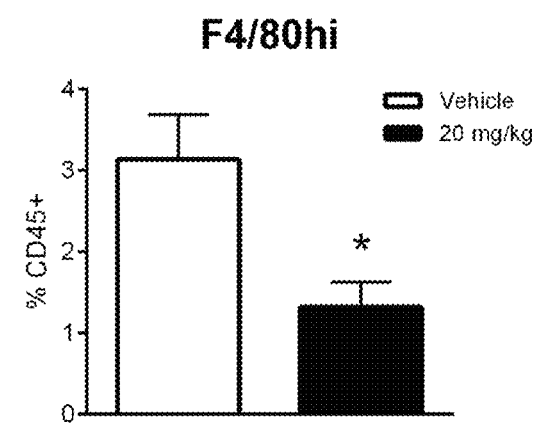
FIG. 9C is a graph showing a decrease in inflammatory macrophages after treatment of an imiquimod induced model of psoriasis with NIM-1001-8.

Oral NIM-1001-8 significantly reduced the proportions of TNF+(FIG. 9A) and IL17+ (FIG. 9B) CD4+ T cells in the spleen relative to vehicle controls. Additionally, NIM-1001-8 decreased the proportion of F4/80hi inflammatory macrophages (FIG. 9C). Statistical significance (P<0.05) is marked by asterisks.

Example 11. Use of NIM-1001-8 in a Model of Sjogren's Syndrome

Introduction

Sjogren's syndrome (SjS) is an autoimmune disease primarily affecting the lacrimal and salivary glands. SjS commonly results from the formation of autoantibodies to one or both of Ro and La leading to focal infiltration in exocrine glands and disorganization of acinar and ductal epithelial cells. Immunologically, SjS is associated with dysfunctional regulatory CD4+ T cells as well as expansion of T helper 1 and T follicular helper cell subsets. The non-obese diabetic (NOD) mouse has been used as a model of Sjogren's syndrome as female mice develop disease of the salivary gland and male mice develop disease of the lacrimal gland spontaneously prior to the onset of hyperglycemia.

Methods

NOD model. Ten-week-old female NOD mice were treated with vehicle or NIM-1001-8 (2 or 50 mg/kg) daily by oral gavage for four weeks. After conclusion of the treatment period, submandibular glands were excised and fixed in formalin. Glands were processed and H&E-stained slides were prepared. Slides were scored by blinded reviewer, on a 0 to 4 composite scale encompassing level of inflammation and disease.

Results

Figure 10:
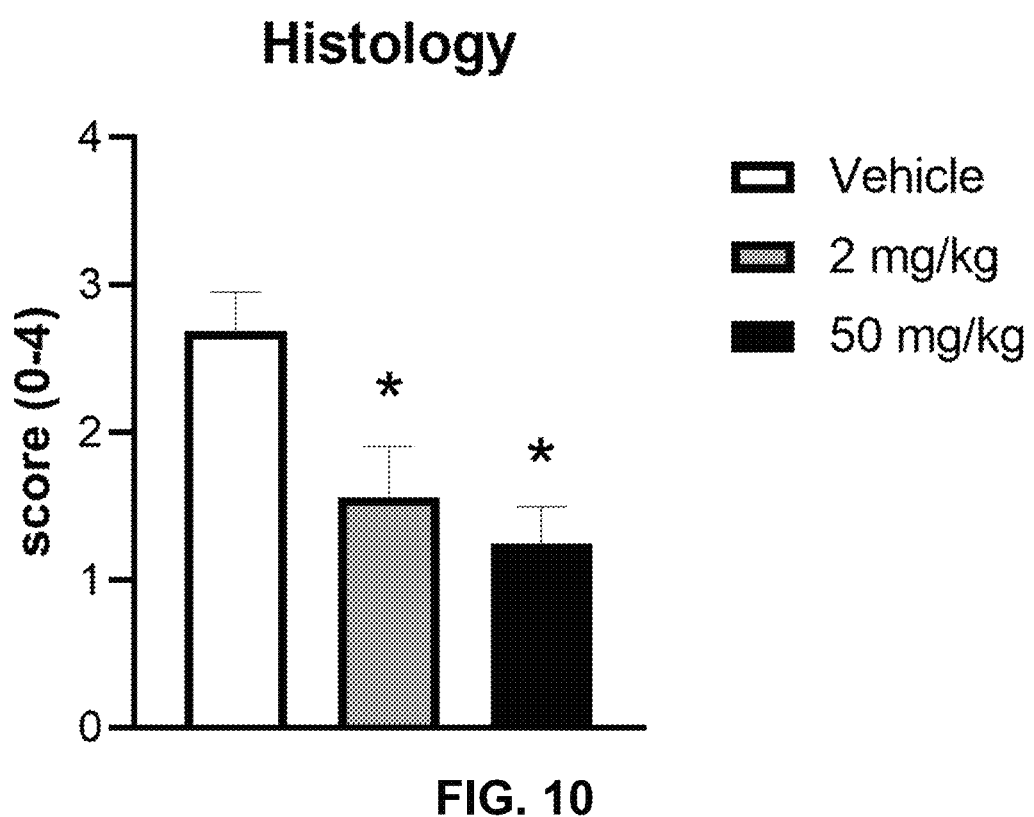
FIG. 10 is a graph showing a decrease in disease severity by blinded histopathological score of submandibular glands after treatment of a spontaneous NOD model of Sjogren's syndrome.

Oral NIM-1001-8 significantly reduced the histological severity of disease in the submandibular glands at both 2 and 50 mg/kg relative to vehicle controls (FIG. 10). Statistical significance (P<0.05) is marked by asterisks.

REFERENCES

Remington's Pharmaceutical Sciences (A.R. Gennaro, Ed.), 20th edition, Williams & Wilkins PA, USA (2000).
US Patent Application Publication 2013/61893613.
U.S. Pat. No. 8,859,546.
U.S. Pat. No. 7,396,943.
PCT Patent Application Publication WO 2005/012298.
PCT Patent Application Publication WO 2015/061247.
PCT Patent Application Publication WO 2021/129817.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A compound selected from any one of Compounds NIM-1001-1 to NIM-1001-39:

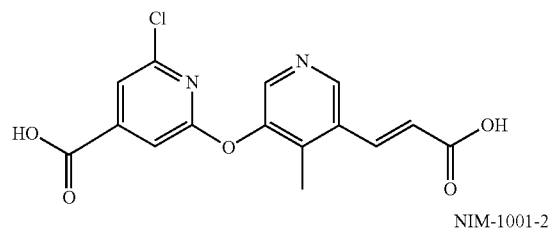

NIM-1001-1

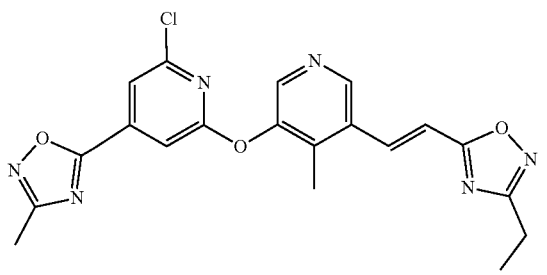

NIM-1001-2

NIM-1001-3
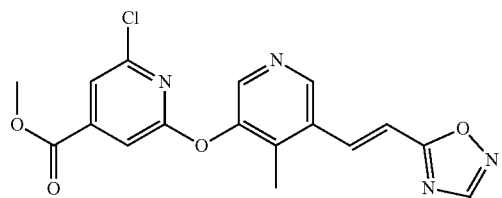
NIM-1001-4
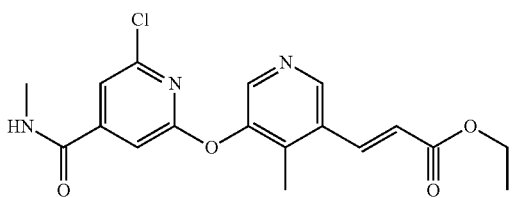
NIM-1001-5
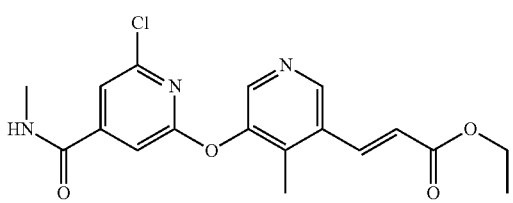
NIM-1001-6
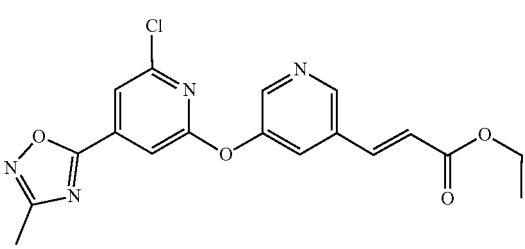
NIM-1001-7
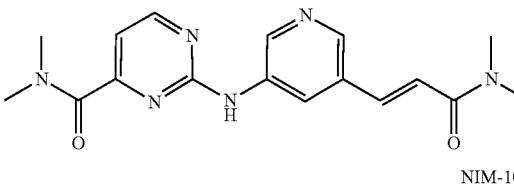
NIM-1001-8
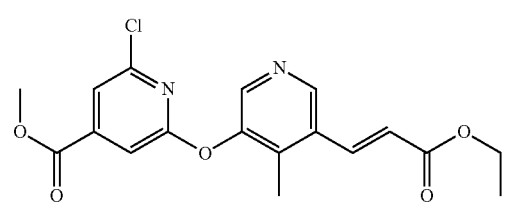
NIM-1001-9
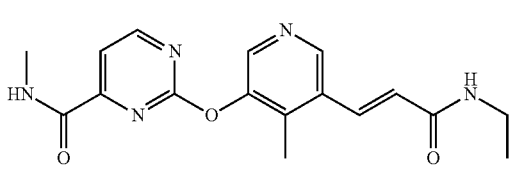
NIM-1001-10
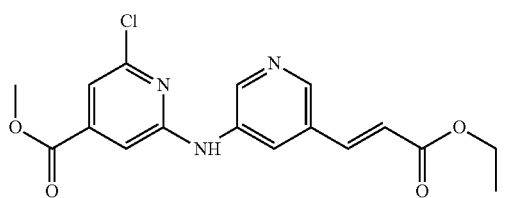
NIM-1001-11
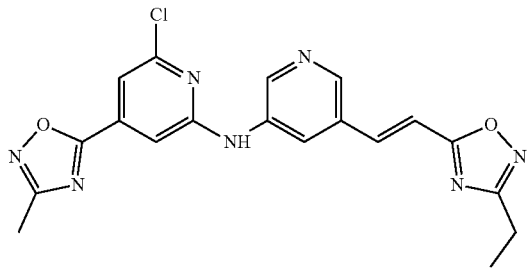
NIM-1001-12
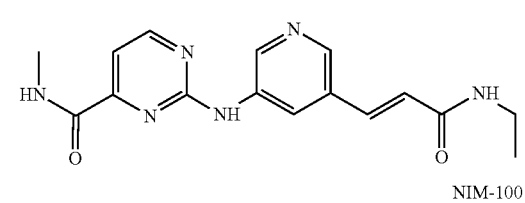
NIM-1001-13
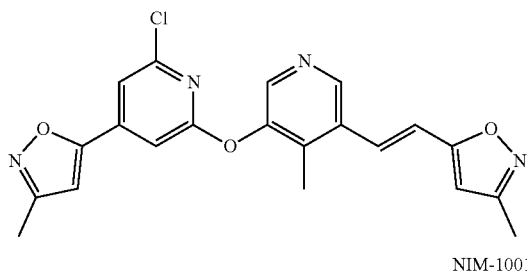
NIM-1001-14
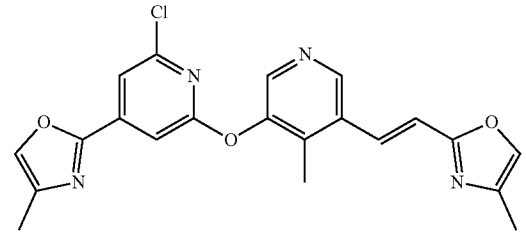
NIM-1001-15
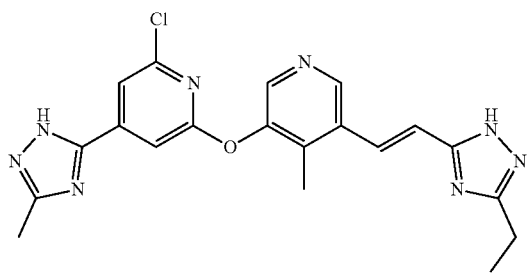

NIM-1001-16

NIM-1001-17

NIM-1001-18

NIM-1001-19

NIM-1001-20

NIM-1001-21

NIM-1001-22

NIM-1001-23

NIM-1001-24

NIM-1001-25

NIM-1001-26

NIM-1001-27

2. The compound of claim 1, in a pharmaceutically acceptable excipient.

3. The compound of claim 2, capable of preventing or reducing severity of an inflammatory disease when administered to a mammal with the disease.

4. The compound of claim 3, wherein the inflammatory disease is systemic inflammation, inflammatory bowel disease, a viral infection that causes inflammation, autoimmune encephalomyelitis, multiple sclerosis, systemic lupus erythematosus, Alzheimer's disease, Parkinson's disease, psoriasis, or Sjogren's disease.

5. The compound of claim 3, wherein the mammal is a human.

6. The compound of claim 2, formulated for administration to a mammal parenterally, enterally, transmucosally, or transdermally.

7. A method of treating a mammal undergoing an inflammatory disease, the method comprising administering the compound of claim 2 to the mammal in a manner sufficient to reduce the severity of the inflammatory disease.

8. The method of claim 7, wherein the inflammatory disease is systemic inflammation, inflammatory bowel disease, a viral infection that causes inflammation, autoimmune encephalomyelitis, multiple sclerosis, systemic lupus erythematosus, Alzheimer's disease, Parkinson's disease, psoriasis, or Sjogren's disease.

9. The method of claim 7, wherein the mammal is a human.

10. The method of claim 7, wherein the compound is formulated for administration to a mammal parenterally, enterally, transmucosally, or transdermally.

\* \* \* \* \*